US005750509A

United States Patent [19]

Malabarba et al.

[11] Patent Number: 5,750,509
[45] Date of Patent: May 12, 1998

[54] AMIDE DERIVATIVES OF ANTIBIOTIC A 40926

[75] Inventors: Adriano Malabarba, Via Roma; Romeo Ciabatti, Via Brodolini; Gianbattista Panzone, Via Vanzago; Alessandra Maria Marazzi, Via Piave, all of Italy

[73] Assignee: Gruppo Lepetit S.p.A., Gerenzano, Italy

[21] Appl. No.: 640,681

[22] Filed: Apr. 30, 1996

Related U.S. Application Data

[63] Continuation of Ser. No. 450,037, May 25, 1995, abandoned, which is a continuation of Ser. No. 370,333, Jan. 9, 1995, abandoned, which is a continuation of Ser. No. 167,809, PCT/EP92/01594 filed Jul. 14, 1992, abandoned.

[30] Foreign Application Priority Data

Jul. 29, 1991 [EP] European Pat. Off. ............ 91112685
Jun. 12, 1992 [EP] European Pat. Off. ............ 92109906

[51] Int. Cl.$^6$ .................... A61K 38/14; C07K 7/50
[52] U.S. Cl. .................... 514/11; 514/9; 514/8; 530/318; 530/345; 530/322; 530/321; 930/190
[58] Field of Search .................... 514/11, 9, 8; 530/317, 530/345, 322, 321; 930/190

[56] References Cited

U.S. PATENT DOCUMENTS

| 4,782,042 | 11/1988 | Selva et al. | 514/9 |
| 4,868,171 | 9/1989 | Selva et al. | 514/183 |
| 4,935,238 | 6/1990 | Selva et al. | 424/118 |
| 5,030,619 | 7/1991 | Hector | 530/317 |

FOREIGN PATENT DOCUMENTS

| 0259781 | 3/1987 | European Pat. Off. . |
| 240609 | 10/1987 | European Pat. Off. . |
| 316712 | 5/1989 | European Pat. Off. . |
| 376041 | 7/1990 | European Pat. Off. . |
| 8802755 | 4/1988 | WIPO . |

OTHER PUBLICATIONS

The Merck Manual of Diagnosis & Therapy, 11th ed. pp. 799–802, (1966).

Malabarbe, et al. The Journal of Antibiotics, pp. 1572–1587, (Nov. 1987).

*Primary Examiner*—Ponnathapura Achutamurthy
*Assistant Examiner*—T. D. Wessendof
*Attorney, Agent, or Firm*—J. Michael Dixon

[57] ABSTRACT

The present invention is directed to novel antibiotic A 40926 derivatives characterized by having a carboxy, ($C_1$–$C_4$) alkoxy-carbonyl, aminocarbonyl, ($C_1$–$C_4$) alkylaminocarbonyl, di ($C_4$–$C_4$)alkylaminocarbonyl or hydroxymethyl substituent on the N-acylaminoglucuronyl moiety and a hydroxy or a polyamine substituent in position 63 of the molecule. The compounds of the invention show high in vitro activity against glycopeptide resistant Enterococci and Staphylococci.

5 Claims, No Drawings

AMIDE DERIVATIVES OF ANTIBIOTIC A 40926

This is a continuation application Ser. No. 08/450,037, filed May 25, 1995, abandoned which is a continuation of application Ser. No. 08/370,333, filed Jan. 9, 1995, now abandoned, which was a continuation of application Ser. No. 08/167,809, filed as PCT/EP92/01594 filed Jul. 14, 1992, now abandoned, which is herein incorporated by reference.

The present invention is directed to antibiotic A 40926 derivatives of formula (I)

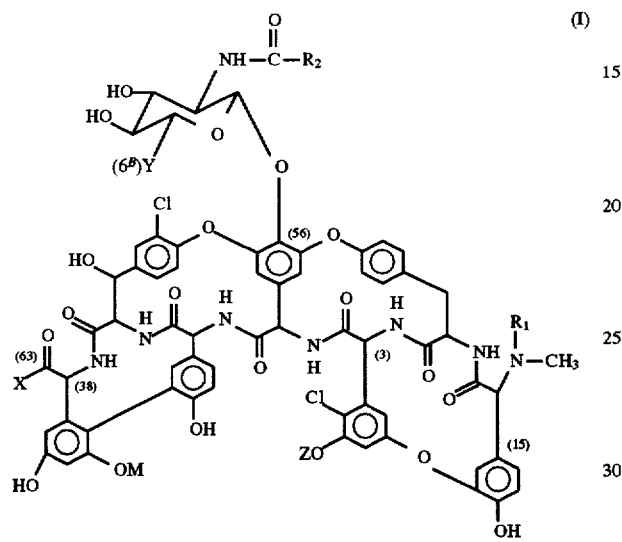

wherein $R_1$ represents hydrogen or a protecting group of the amino function;

$R_2$ represents $(C_9-C_{12})$alkyl;

M represents hydrogen, α-D-mannopyranosyl or 6-O-acetyl-α-D-mannopyranosyl;

Y represents carboxy, $(C_1-C_4)$alkoxycarbonyl, aminocarbonyl, $(C_1-C_4)$alkylaminocarbonyl, di$(C_1-C_4)$alkylaminocarbonyl wherein the alkyl moitety may bear a substituent selected from hydroxy, amino, $(C_1-C_4)$alkylamino and di$(C_1-C_4)$alkylamino or hydroxymethyl;

x represents hydroxy or an amino rest of formula

—NR$_3$—alk$_1$—(NR$_4$—alk$_2$)$_p$—(NR$_5$—alk$_3$)$_q$—W wherein:

$R_3$ represents hydrogen or $(C_1-C_4)$alkyl;

alk$_1$, alk$_2$ and alk$_3$ each independently represent a linear or branched alkylene of 2 to 10 carbon atoms;

p and q are integers which independently represent zero or 1;

$R_4$ and $R_5$ each independently represent hydrogen, $(C_1-C_4)$alkyl or $R_3$ and $R_4$ taken together represent a $(C_2-C_4)$alkylene moiety connecting the two nitrogen atoms with the proviso that p is 1; or $R_4$ and $R_5$ taken together represent a $(C_2-C_4)$alkylene moiety connecting the two nitrogen atoms with the proviso that both p and q are 1;

w represents hydrogen, $(C_1-C_4)$alkyl, amino, $(C_1-C_4)$alkylamino, di$(C_1-C_4)$alkylamino, amino substituted with one or two amino-$(C_2-C_4)$alkyl moieties or with one or two $(C_1-C_4)$alkylamino-$(C_2-C_4)$alkyl moieties or with one or two di$(C_1-C_4)$alkylamino-$(C_2-C_4)$alkyl moieties, or, when both p and q are zero, taken together with the moiety —NR$_3$—alk$_1$— it may also represent piperazino or 4-methylpiperazino, with the proviso that when X represents hydroxy Y represents hydroxymethyl, z represents hydrogen or a group

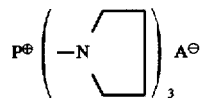

wherein $A^\ominus$ represents a mineral or organic acid anion or, when a carboxyacid function is present in the remaining portion of the antibiotic, it may also represent the internal anion deriving from said carboxyacid function;

and the pharmaceutically acceptable addition salts thereof. The number between brackets in the above formula (I) and in any successive formula indicate the conventional numbering of the relative carbon atoms in the molecular structure of antibiotic A-40926 and its derivatives.

Antibiotic A 40926 is a glycopeptide antibiotic complex which has been isolated from a culture of *Actinomadura*, named *Actinomadura* sp. ATCC 39727, in a culture medium containing assimilable sources of carbon, nitrogen, and inorganic salts (see EP-177882). According to the procedure described in the above cited patent the recovery of the antibiotic complex, whose factors have been named factor A, factor B, factor B$_0$, factor B$_1$, factor PA, and factor PB, includes submitting the fermentation broths, after filtration or after a preliminary purification, to affinity chromatography on immobilized D-alanyl-D-alanine.

The A 40926 factors can be represented by formula (II) below wherein R'$_1$ is hydrogen, X' is hydroxy, Y' is carboxy, R'$_2$ represents a $(C_9-C_{12})$alkyl group, and M' represents an α-D-mannopyranosyl or a 6-O-acetyl-α-D-mannopyranosyl group.

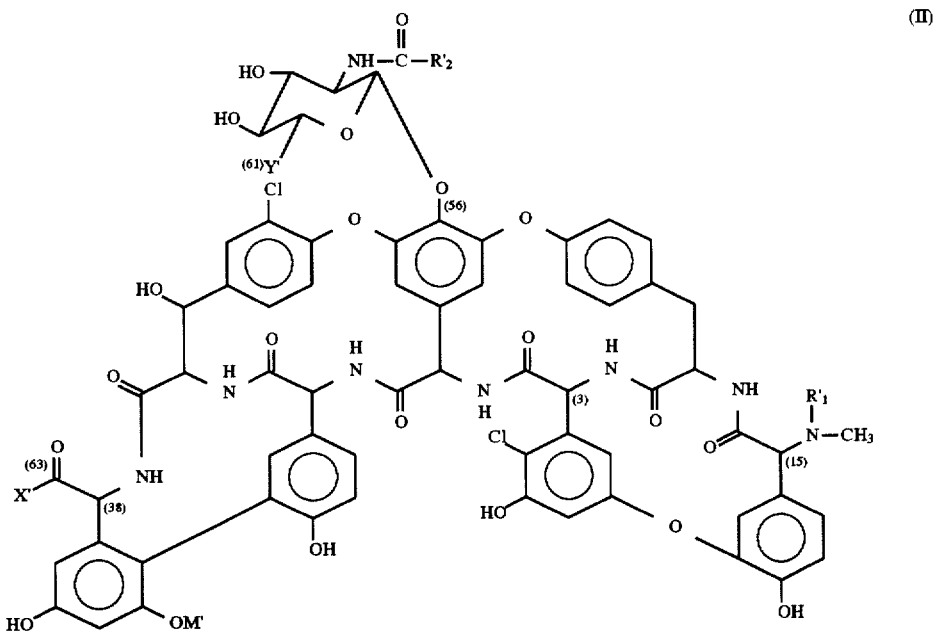

(II)

More particularly, antibiotic A 40926 factor A is a compound of the above formula (II) wherein $R'_1$ is hydrogen, X' is hydroxy, Y' is carboxy, $R'_2$ represents n-decyl and M' represents α-D-mannopyranosyl. According to the most recent studies, the substance identified as antibiotic A 40926 B in the above mentioned EP-177882 actually consists of two closely related components. Antibiotic A 40926 factor $B_0$ is indeed the main component of factor B, and corresponds to the compound of the above formula (II) wherein $R'_1$ is hydrogen, X' is hydroxy, Y' is carboxy, $R'_2$ represents 9-methyldecyl and M' represents α-D-mannopyranosyl. The minor component of factor B is named factor $B_1$ and differs from factor $B_0$ only in that $R'_2$ represents n-undecyl (E. Riva et al, Chromatographia, Vol. 24, 295, 1987).

Antibiotic A 40926 factor PA and factor PB differ from the corresponding factor A and B in that the mannose unit is replaced by a 6-O-acetyl-α-D-manno-pyranose unit.

Antibiotic A 40926 factors PA and PB, at least under certain fermentation conditions, are the main antibiotic products of the A 40926 producing microorganism.

Antibiotic A 40926 factors A and B are mainly transformation products of antibiotics A 40926 factor PA and factor PB, respectively, and are often already present in the fermentation broths.

All the sugar moieties are linked to the antibiotic A 40926 nucleus through O-glycosidic bonds.

It has been found that antibiotic A 40926 factor PA can be transformed into antibiotic A 40926 factor A and antibiotic A 40926 factor PB can be transformed into antibiotic A 40926 factor B under basic conditions which lead to the removal of the acetyl group of the mannose unit without displacing the acyl group on the aminoglucuronyl unit.

As a consequence, when the fermentation broth or an antibiotic A 40926 containing extract or concentrate thereof, is allowed to stand for a certain time under basic conditions (e.g. aqueous solution of a nucleophilic base, at a pH>9 overnight) an antibiotic A 40926 complex is obtained which is enriched in antibiotics A 40926 factor A and factor B.

Antibiotic A 40926 factor B can be obtained from A 40926 complex by chromatographic separation using the method described in EP-177882. Pure factor $B_0$ which under the conditions described in the above mentioned European Patent account for about 90% of factor B, can be obtained by further purification of factor B, for instance, by repeated reverse-phase chromatography procedures.

More recent studies (L. Zerilli et al., Rapid Communications in Mass Spectrometry, Vol. 6, 109, 1992) have shown that in the antibiotic complex A 40926 are present also some minor factors which are identified with the acronyms $A_1$, RS-1, RS-2 and RS-3, respectively. These minor factors have been individuated by HPLC and their structures have been determined by applying gas chromatography/mass spectrometry analysis to the methanolysates of the A-40926 complex. All the above mentioned minor factors have structures corresponding to the basic structure of factor A, $B_0$ and $B_1$ apart from the fatty acid residues linked to the aminoglucuronic moiety. More preferably, making reference to the formula (II), $R'_1$, X' and Y' have the same meanings as above while $R'_2$ represents:

8-methylnonyl in factor $A_1$, 7-methyloctyl in factor RS-1, n-nonyl in factor RS-2 and n-dodecyl in factor RS-3.

Although in the antibiotic A 40926 complex preparations currently obtained by following the fermentation conditions described in EP 177882 the factors wherein $R'_2$ is a $(C_{10}-C_{11})$alkyl are largely predominant, it is possible to modify the fermentation conditions to increase the amounts of the minor components wherein $R'_2$ is a $C_9$ or a $C_{12}$ alkyl.

During the usual purification procedures of antibiotic A 40926 complex, factors PA and PB are largely converted to factors A and B.

In addition, it has been found that it is possible to transform antibiotic A 40926 complex, its single factors or a mixture of said factors in any proportion into the corresponding N-acylaminoglucuronyl aglycone complex AB, N-acylaminoglucuronyl aglycone factor A, N-acylaminoglucuronyl aglycone factor B, and the mannosyl aglycone of A 40926 by controlled acid hydrolysis of one of the sugar moieties of the starting material(see EP-A-240609 and EP-A-228015).

Preferred hydrolysis conditions for the production of N-acylaminoglucuronyl aglycones comprise the usage of a mixture of dimethylsulfoxide/concentrated hydrochloric acid from 8:2 to 9.5:0.5 at a temperature between 40° C. and 80° C.

Antibiotic A 40926 N-acylaminoglucuronyl aglycones are represented by the above formula (II) wherein $R'_1$ and M' are hydrogen atoms, X' is hydroxy, Y' is carboxy and $R'_2$ is $(C_9-C_{12})$alkyl.

The complete cleavage of all the sugar moieties of the A 40926 antibiotics gives the aglycone. This hydrolysis process is described in EP-A-240609.

Antibiotic A 40926 complex, the factors thereof, the corresponding N-acylaminoglucuronyl aglycones, the mannosyl aglycone, the aglycone, and mixtures thereof in any proportion are mainly active against gram positive bacteria and Neisseriae.

In the International Patent Application No. PCT/EP92/00374 claiming the priority of EP Ser. No. 91104857 the ester derivatives (esterified at the position $6^B$, that is the carboxy group present on the N-acylamino glucuronyl moiety) of antibiotic A 40926 and its N-acyl-aminoglucuronyl aglycone are described; i.e. the compounds of formula (II) wherein X' is OH, Y' is $(C_1-C_4)$ alkoxycarbonyl and $R'_1$, $R'_2$ and M' have the same meanings of the symbols $R_1$, $R_2$ and M above. These ester derivatives are prepared by reacting the $N^{15}$-protected (in this description the term "$N^{15}$" refers to the nitrogen atom of the amino function attached to the carbon atom of A 40926 molecule conventionally designated with the number 15) or $N^{15}$-free amino A 40926 substrate or its demannosyl derivative (i.e. N-acylaminoglucuronyl aglycone) with an alkanol in an acid medium, or a $N^{15}$-protected A 40926 derivative or its demannosyl analogue with an alkyl halide (preferably bromide, chloride or iodide), optionally, in the presence of an hydrohalic acid acceptor, in particular, with an excess of the selected alkanol in the presence of concentrated mineral acid at a temperature between 0° C. and room temperature.

These ester derivatives of antibiotic A 40926 prepared according to the method mentioned above are employed as starting materials for the preparation of the antibiotic A 40926 derivatives of formula (I).

As outlined above, controlled esterification procedures useful for preparing A 40926 ester derivatives and demannosyl A 40926 ester derivatives which are starting materials of the compounds of this invention include esterification reactions wherein the A 40926 substrate is brought together with an excess of the selected alkanol in the presence of concentrated mineral acid at a temperature between 0° C. and room temperature for a time varying with the steric complexity of the group that must be introduced.

In some instances it is convenient to protect the primary amino function in position 15 of the A 40926 precursor in order to reduce possible undesired side-reactions. This can be done by methods known per se in the art such as those described in reference books like T. W. Greene, "Protective Groups in Organic Synthesis", John Wiley and Sons, New York, 1981 and M. Mc Omie "protecting Groups in Organic Chemistry" Plenum Press, New York, 1973. These protecting groups must be stable at the conditions of the reaction process, must not unfavourably interfere with the main reaction, and must be easily cleavable at the end of the main reaction.

The tert-butoxycarbonyl (t-BOC), carbobenzyloxy (CBz), and arylalkyl groups are examples of suitable amino protecting groups. The benzylation with optionally substituted benzyl halides in the presence of a base takes place smoothly with quantitative yield and leads exclusively to the formation of the corresponding $N^{15}$-benzyl derivative without the concomitant formation of a benzyl ester of the carboxy groups.

Selective protection of the amino group at position 15 may be preferably carried out by reaction with benzyl bromide in the presence of an hydrogen halide acceptor (i.e. a tertiary amine) without concomitant esterification of the two carboxy groups.

The conditions of removal of the $N_{15}$-protecting groups are falling within those known in the art for the removal of the amino protecting groups and must be set up after an evaluation of the reactivity of other groups present in the molecule.

An ester starting compound of formula (II) wherein M' is α-D-mannopyranosyl or 6-O-acetyl-α-D-mannopyranosyl, and Y' is $(C_1-C_4)$alkoxycarbonyl can be transformed into the corresponding compound wherein M'is hydrogen by means of selective acid hydrolysis. As disclosed in EP-A-240609 preferred hydrolysis conditions for the production of demannosyl derivatives of antibiotic A 40926 (e.g.: N-acylaminoglucuronyl aglycone) comprises the usage of a mixture of dimethylsulfoxide/concentrated hydrochloric acid from 8:2 (v/v) to 9.5:0.5 (v/v) at a temperature between 40° and 80° C.

Accordingly, the demannosyl derivatives of the esters of A 40926 can be obtained in a mixture with the corresponding A 40926 aglycone and can be separated by preparative HPLC.

The hydrolytic conditions may be suitably modified to change the ratio between the resulting products. For instance, starting from A 40926 esterified in position $6^B$, by increasing the solvent/hydrochloric acid ratio to 78:1, keeping the reaction temperature below 60° C. and increasing the reaction time to about 7 days, the ratio of the desired demannosyl derivatives of A 40926 esterified at position $6^B$ to the undesired aglycone of A 40926 results of about 1.4:1.0.

The reaction courses are monitored by HPLC according to methods known in the art. On the basis of the results of these assays, a man skilled in the art will be able to evaluate the reaction course and decide when to stop the reaction and start working up the reaction mass according to known per se techniques which include, for instance, extraction with solvents, precipitation by non-solvents, in conjunction with further separation and purification by chromatography.

The ester derivatives used as starting materials for the preparation of the compounds of formula (I) may be single compounds corresponding to each of the several factors of the precursor antibiotic A 40926 complex or mixtures of two or more components in any proportion, corresponding to the different factors of the A 40926 precursor. Said mixtures of ester derivatives may result by the use of the A-40926 complex or a mixture of the factors of the A 40926 complex precursor in the manufacture of the $6^B$ ester or by applying particular conditions in the isolation/purification of the resulting ester product (which may alter the original proportions of the factors characterizing the precursor A 40926 complex) or by mixing in the appropriate proportions the pure ester products isolated by reverse-phase chromatography separation procedures or obtained by using the pure A 40926 factors as the precursors.

In this description and claims, when it is not otherwise specified, the term "alkyl", either alone or in combination with other substituents, includes both straight and branched hydrocarbon groups; more particularly, the term "$(C_1-C_4)$ alkyl" represents a straight or branched aliphatic hydrocarbon chain of 1 to 4 carbon atoms such as methyl, ethyl, propyl, 1-methylethyl, butyl, 1-methylpropyl, 1,1-dimethylethyl, and 2-methylpropyl.

As used herein the terms "$alk_1$", "$alk_2$", "$alk_3$", represent an independent linear or branched alkylene chain of 2 to 10 carbon atoms such as for example;

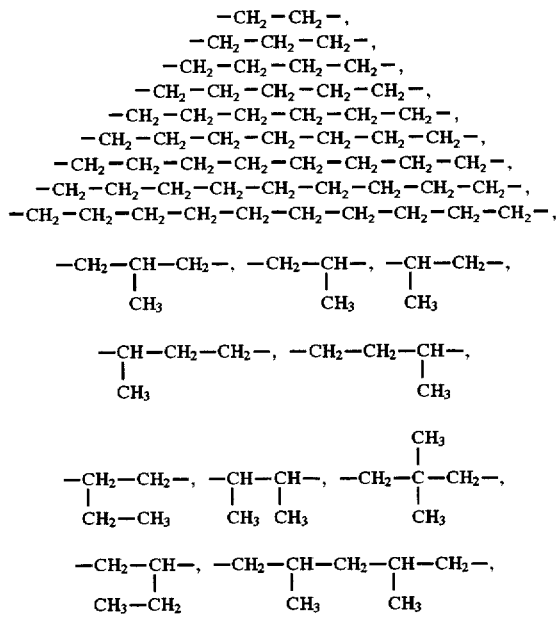
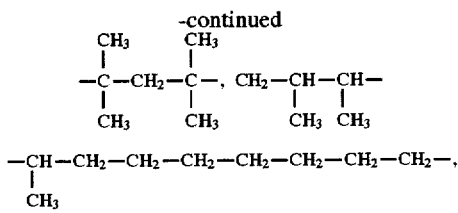

The terms "(C₂–C₄)alkyl moieties" and "(C₂–C₄)alkylene moiety" as used herein represent a linear or branched aliphatic chain rest of 2 to 4 carbon atoms. Representative examples of said chains can be drawn from the above list.

The expression "(C₁–C₄)alkoxycarbonyl" includes both straight and branched alkoxycarbonyl groups such as for instance methoxycarbonyl, ethoxycarbonyl, propyloxycarbonyl, isopropyloxycarbonyl, butoxycarbonyl, isobutoxycarbonyl, and tert-butoxycarbonyl.

Here below are given some representative examples of the amino rest

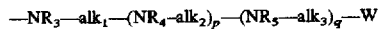

according to the above definition:

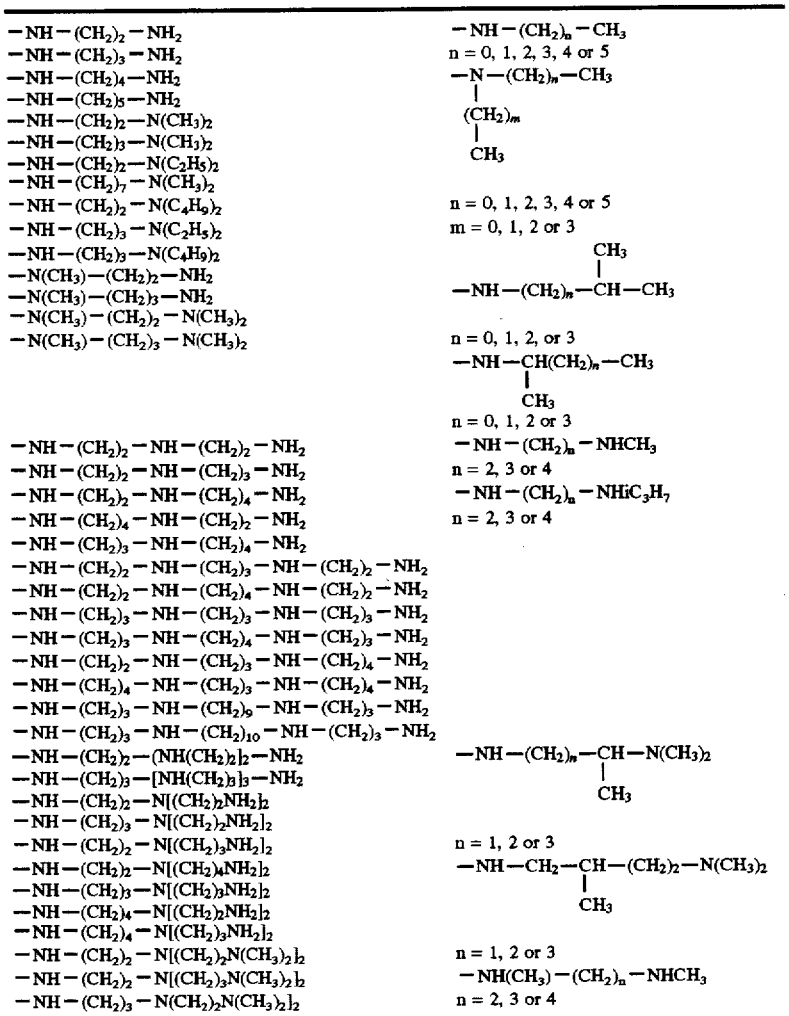

-continued

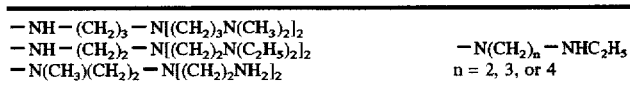

and the like.

When $R_3$ and $R_4$ (or $R_4$ and $R_5$) taken together represent a $(C_2-C_4)$alkylene moiety connecting the two nitrogen atoms, the saturated heterocyclic moiety formed in combination with the portions $alk_1$ (or $alk_2$) and the two adjacent nitrogen atoms is preferably a piperazino ring.

For example, when $R_3$ and $R_4$ (or $R_4$ and $R_5$) taken together represent a $(C_2-C_4)$alkylene moiety connecting the two nitrogen atoms or when, both p and q being zero, W taken together with the moiety —$NR_3$—$alk_1$— represents piperazino or 4-methylpiperazino, the amino rest of formula:

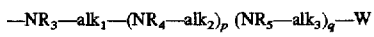

identifies the following groups:

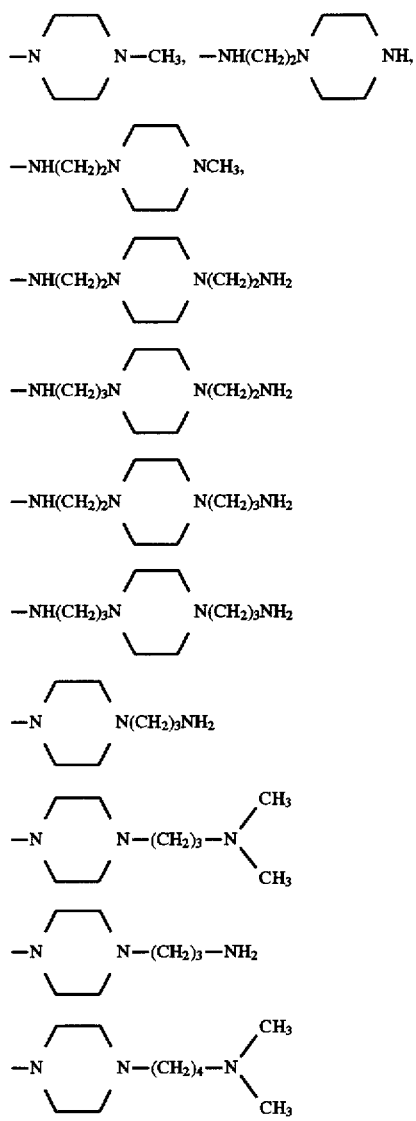

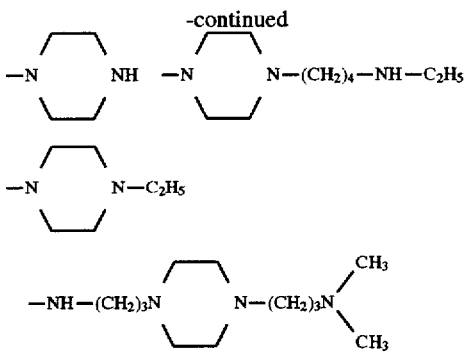

The scope of this invention comprises the unitary compounds of formula (I) which derive from the single factors of the precursor antibiotic A 40926 complex as well as the mixtures of compounds of formula (I) deriving from the complex A 40926 itself or from the mixtures of two or more of its factors in any proportion. Accordingly, the variation of the mutual proportions of the components of the mixtures of compounds of formula (I) corresponding to the factors of A 40926 complex can result from applying different conditions in the fermentation, recovery, isolation and purification conditions of the precursor antibiotic A 40926 complex or by mixing the isolated factors of the starting esters of formula (II) in the desired proportions before their conversion to compounds of formula (I) or by mixing the pure individual factors of the invention compounds of formula (I) in the desired proportions.

Preferred compounds of formula (I) are those wherein $R_1$ represents hydrogen or a protecting group of the amino function;

$R_2$ represents $(C_9-C_{12})$alkyl;

M represents hydrogen, α-D-mannopyranosyl or 6-O-acetyl-α-D-mannopyranosyl;

Y represents represents carboxy, $(C_1-C_4)$alkoxycarbonyl, aminocarbonyl, $(C_1-C_4)$alkylaminocarbonyl, di$(C_1-C_4)$alkylaminocarbonyl wherein the alkyl moitety may bear a substituent selected from hydroxy, amino, $(C_1-C_4)$alkylamino and di$(C_1-C_4)$alkylamino or hydroxymethyl;

x represents hydroxy or an amino rest of formula

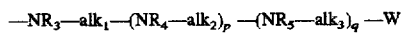

wherein $R_3$, $R_4$ and $R_5$ represent hydrogen;

$alk_1$, $alk_2$, and $alk_3$ each independently represents a linear or branched alkylene of 2 to 4 carbon atoms.

p and q are integers which independently represent zero or 1;

W represents hydrogen, $(C_1-C_4)$alkyl, amino, $(C_1-C_4)$alkylamino, di$(C_1-C_4)$alkylamino, amino substituted with one or two amino-$(C_2-C_4)$ alkyl moieties or with one or two $(C_1-C_4)$alkylamino-$(C_2-C_4)$alkyl moieties or with one or two di$(C_1-C_4)$alkylamino- ($C_2$-$C_4$)alkyl moieties, or, when both p and q are zero, taken together with the moiety —$NR_3$—$alk_1$— it may also represent piperazino or 4-methylpiperazino with the proviso that when X represents hydroxy Y represents hydroxymethyl;

z represents hydrogen or a group

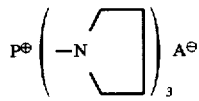

wherein $A^⊖$ represents a mineral or organic acid anion or, when a carboxyacid function is present in the remaining portion of the antibiotic, it may also represent the internal anion deriving from said carboxyacid function;

and the pharmaceutically acceptable addition salts thereof.

Another preferred group of compounds of the invention comprises those derivatives of formula (I) wherein $R_2$ represents, ($C_{10}$-$C_{11}$)alkyl, M represents α-D-mannopyranosyl and $R_1$, X, Y and Z are described as herein above, and the pharmacetically acceptable addition salts thereof.

A further preferred group of compounds of the present invention encompasses those compounds of formula (I) wherein:

$R_1$ represents hydrogen or a protecting group of the amino function, preferbly hydrogen;

$R_2$ represents 7-methyloctyl, n-nonyl, 8-methylnonyl, n-decyl, 9-methyldecyl, n-undecyl or n-dodecyl, preferably n-decyl, 9-methyldecyl or n-undecyl, most preferably 9-methyldecyl;

M is hydrogen or α-D-mannopyranosyl, preferably α-D-mannopyranosyl;

y represents carboxy, ($C_1$-$C_4$)alkoxycarbonyl, aminocarbonyl, ($C_1$-$C_4$)alkylaminocarbonyl, di($C_1$-$C_4$)alkylaminocarbonyl wherein the alkyl moitety may bear a substituent selected from hydroxy, amino, ($C_1$-$C_4$)alkylamino and di($C_1$-$C_4$)alkylamino or hydroxymethyl, preferably carboxy, methoxycarbonyl, aminocarbonyl, methylaminocarbonyl, dimethylaminocarbonyl, (dimethylamino)ethylaminocarbonyl or hydroxymethyl;

X is an amino rest

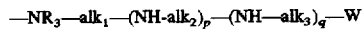

wherein:

$R_3$ is hydrogen;

$alk_1$, $alk_2$ and $alk_3$ each independently represents a linear alkylene of 2 to 4 carbon atoms;

p and q each independently represent zero or 1; and w represents amino, ($C_1$-$C_4$)alkylamino, di-($C_1$-$C_4$) alkylamino, amino substituted with one or two amino-($C_2$-$C_4$)alkyl moieties or, when both p and q are zero, taken together with the moiety —$NR_3$— $alk_1$ it may also represent piperazino or 4-methylpiperazino;

most preferably, X is an amino rest selected from:

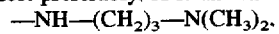

—NH—($CH_2$)$_3$—N[($CH_2$)$_3$ $NH_2$]$_2$ and

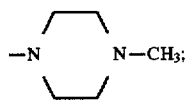

z represents hydrogen; and the pharmaceutically acceptable addition salts thereof.

The compounds of formula (I) wherein Y is ($C_1$-$C_4$) alkoxycarbonyl, $R_1$, $R_2$, M and Z are as specified at the beginning of this description and X represents an amino rest

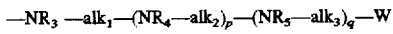

wherein $R_3$ $R_4$, $R_5$, $alk_1$, $alk_2$, $alk_3$, p, q, and W are as specified at the beginning of this description, are prepared by amidation of the corresponding derivatives of formula (II) above wherein $R'_1$, $R'_2$ and M' have the same meanings as $R_1$, $R_2$ and M, X' is hydroxy and Y' is ($C_1$-$C_4$)alkoxycarbonyl.

These starting materials of formula (II) are prepared as described above and some specific examples thereof are disclosed in the already mentioned International Patent Application PCT/EP92/00374. The amidation procedure involves condensing said starting materials of formula (II) with an appropriate amine of the formula (III):

 (III)

wherein $R_3$, $R_4$, $R_5$, $alk_1$, $alk_2$, $alk_3$, p, q and W have the same meanings as specified at the beginning of this description, in the presence of a condensing agent or via formation of an "activated ester" of the said starting $C_{63}$ carboxylic acid of formula (II) in an inert organic solvent.

Inert organic solvents useful for the amidation reaction are those organic aprotic solvents which do not unfavourably interfere with the reaction course and are capable of at least partially solubilizing the starting material.

Examples of said inert organic solvents are organic amides, ethers of glycols and polyols, phosphoramides and sulfoxides. Preferred examples of inert organic solvents are: dimethylformamide, dimethoxyethane, hexamethylphosphoramide, dimethylsulfoxide and mixtures thereof.

The condensing agent in the process of the invention is one suitable for forming amide bonds in organic compounds and in particular in peptide synthesis.

Representative examples of condensing agents are diisopropylcarbodiimide (DIC), dicylcohexylcarbodiimide (DCC) in the presence of hydroxybenzotriazole (HBT), benzotriazolyloxy-tris-(dimethylamino)phosphonium hexafluorophosphate, benzotriazolyloxy-tris-(pyrrolidino) phosphonium hexafluorophosphate and ($C_1$-$C_4$)alkyl, phenyl or heterocyclic phosphorazidates such as, diphenyl phosphorazidate, diethyl phosphorazidate, di-(4-nitrophenyl)phosphorazidate, dimorpholylphosphorazidate and diphenylphosphorochloridate. The preferred condensing agents are diphenyl phosphorazidate, i.e. phosphoric acid diphenyl ester azide (DPPA), benzotriazolyloxy-tris-(dimethylamino)phosphonium hexafluorophosphate (BOP), and benzotriazolyloxy-tris-(pyrrolidino)phosphonium hexafluorophosphate (PyBOP).

Between the two last mentioned condensing agents PyBOP is particularly preferred since the resulting by-product pyrrolidine has less potential toxicity problems than dimethylamine.

In the amidation process of the invention described here, the amine reactant is normally used in a molar excess, although in some cases the reaction may be carried out with good yields by using the amine reactant in equimolecular proportion or in a slight molar excess, in particular, when using BOP or PyBOP as condensing agents.

In general, when the amine reactant is a fairly unexpensive or easily obtainable reactant, a 2- to 10-fold molar excess of amine (III) is used while a 3 to 4-fold molar excess is preferred.

For carrying out the amidation of the above mentioned starting material of formula (II) with the amine (III) in the presence of a condensing agent, it is necessary that the amine reactant be capable of forming a salt with the carboxy function (X'=hydroxy) of said starting material. In case the amine is not strong enough to form such a salt in the selected reaction medium, it is necessary to add a salt-forming base (e.g. a tertiary aliphatic or heterocyclic amine, such as triethylamine, N-methylpyrrolidine or N-methyl-piperazine, which cannot form an amide bond with the carboxy function) to the reaction mixture in an at least equimolecular amount with respect to the starting material.

Use of a low molar excess of the amine reactant with addition of a salt-forming base is a suitable method when the amine reactant is a rather expensive or hardly obtainable product.

Examples of said salt-forming bases are tertiary organic aliphatic or heterocyclic amines such as trimethylamine, triethylamine, N-methyl pyrrolidine or picoline, and the like.

The condensing agent is generally employed in an equimolecular amount or a slight molar excess such as from 1.1 to 1.7 times and preferably 1.2 to 1.5 times over the starting A 40926 compound. In particular, it has been observed that with starting materials of formula (II) wherein Y' is ($C_1$–$C_4$)alkoxycarbonyl, when using a large excess (e.g. 3-fold molar excess) of PyBOP as condensing agent and a large excess of the amine reactant (e.g. 6 to 10-fold molar excess), amide end products of formula (I) wherein Z represents

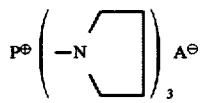

wherein $A_\ominus$ has the same meaning as above are obtained in almost quantitative yields.

The amine reactant may also be conveniently introduced in the reaction medium as a corresponding acid addition salt, e.g. the hydrochloride. In this case, at least a double molar proportion and preferably a 2 to 4 fold molar excess of a strong base capable of freeing the amine from its salts, is added. Also in this case, the suitable base is usually a tertiary organic aliphatic or heterocyclic amine which cannot form an amide bond with carboxy function like those exemplified above. In fact, at least in some instances, the use of a salt of the amine which is then freed in situ with the above mentioned bases, is highly preferred, especially when the salt is more stable than the corresponding free amine.

The reaction temperature will vary considerably depending on the specific starting materials and reaction conditions. In general, it is preferred to conduct the reaction at temperature between 0°–30° C.

Also the reaction time will vary considerably depending on the condensing agent and the other reaction parameters. In general, the condensation reaction is completed within a period of time from about one hour to about 24–48 hours.

In any case, the reaction course is monitored by TLC or, preferably, by HPLC according to methods known in the art.

On the basis of the results of these assays a man skilled in the art will be able to evaluate the reaction course and decide when to stop the reaction and start working up the reaction mass according to known per se techniques which include, for instance, extraction with solvents, precipitation by addition of non-solvents, etc., in conjunction with further common separation operations and purifications, e.g. by column chromatography.

Usually, when using condensing agents like those mentioned above it is not necessary to protect the $N^{15}$-amino function of the starting ester of formula (II). However, it may be useful to utilize starting esters protected on such function when they directly result from the preceeding reaction step whereby said esters are prepared from the precursor antibiotic A 40926. Moreover, there may be specific cases where the amidation reaction conditions make necessary or, at least preferable to protect the $N^{15}$-amino function on the starting ester of formula (II).

In said cases the $N^{15}$-amino function can be protected by methods known per se in the art such as those described in the reference books suggested above for the protection of the A 40926 precursor for the preparation of the esters of formula (II) wherein Y' is ($C_1$–$C_4$)alkoxycarbonyl.

The N-protecting groups must be stable at the conditions of the reaction process, must not unfavourably interfere with the amidation reaction, and must be easily cleavable and removable from the reaction medium at the end of the reaction without altering the newly formed amide bond and the overall structure of the compounds, e.g. the sugar moieties.

Representative examples of N-protecting groups which may be advantageously used in the process of the invention for protecting the $N^{15}$-primary amino function of the ester starting material and, when appropriate, any other amino function(s) optionally characterizing the amine (III) which should not be involved in the amidation reaction, are carbamate forming reagents characterized by the following oxycarbonyl groups: 1,1-dimethylpropynyloxycarbonyl, t-butyloxycarbonyl, vinyloxycarbonyl, cinnamyloxycarbonyl, benzyloxycarbonyl, p-nitrobenzyloxycarbonyl, 3,4-dime-thoxy-6-nitrobenzyloxycarbonyl, 2,4-dichlorobenzyloxy-carbonyl, 5-benzisoxazolylmethyloxycarbonyl, 9-anthranylmethyloxycarbonyl, diphenylmethyloxycarbonyl, isonicotinoyloxycarbonyl, diphenylmethyloxycarbonyl, S-benzyloxycarbonyl, and the like.

Generally, these protecting groups are removable when the amidation reaction is complete by treatment with neat strong organic acids such as trifluoroacetic acid (TFA) and with diluted mineral acids. In order to avoid the risk to hydrolyze the sugar moieties attached to the core of the antibiotic molecule is also possible to remove some of the protecting groups under different removal conditions, such as catalytic hydrogenation, using, for instance, Palladium on carbon as a catalyst. Otherwise, it is possible to remove the amino protecting groups, selected among those reported above, under controlled acidic conditions, e.g. low temperatures and/or short reaction times.

When the amidation reaction is carried out through the intermediate formation of an "activated ester" of the starting compound of formula (II), such "activated ester" is generally formed in situ or, alternatively, it may be isolated and then reacted with the amine of formula (III). The starting material of formula (II) is preferably protected on the $N^{15}$-amino function to avoid any interference of the activating ester forming reagent with the $N^5$-amino group. Protection of such group can be achieved according to known methods and procedures as described above.

The formation of "activated esters" of carboxylic acids is described in general terms in Fieser and Fieser, Reagent for organic synthesis, John Wiley and Sons Inc., pages 129-130 (1967).

Examples of said activated ester forming reagents that can be conveniently used in the process of the invention are those described by R. Schwyzer et al. in Belv. Chim. Acta, 1955, 38, 69-70 and encompass those ester derivatives of formula (II) in which X' is $CH_2CN$, $CH_2COOC_2H_5$, $CH_2(COOC_2H_5)_2$, $CH_2COCH_3$,

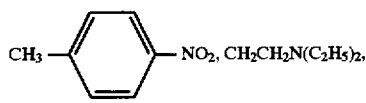

which can be prepared from a starting material of formula (II), wherein $R'_1$ is a suitable protecting group and X' is hydroxy, by reaction with $ClCH_2CN$, $BrCH_2COOC_2H_5$, $BrCH(COOC_2H_5)_2$, $ClCH_2COCH_3$,

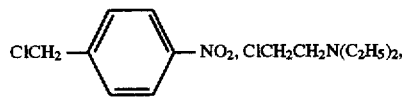

respectively, in the presence of an acid acceptor in a solvent.

A preferred reagent of this type is chloroacetonitrile. In this case, chloroacetonitrile itself, dimethylformamide (DMF) or dimethylsulfoxide (DMSO) can be used as preferred solvents.

Generally, inert organic solvents useful for the formation of "activated esters" are those organic aprotic solvents which do not unfavorably interfere with the reaction course and are capable of, at least partially, solubilizing the carboxyacid starting material.

Examples of said inert organic solvents are organic amides, ethers of glycols and polyols, phosphoramides, sulfoxides and aromatic compounds. Preferred examples of inert organic solvents are: dimethylformamide, dimethoxyethane, hexamethylphosphoramide, dimethylsulfoxide, benzene, toluene and mixtures thereof.

More preferably, the solvent is selected from acetonitrile, dimethylsulfoxide, dimethylformamide. The formation of the activated ester is generally conducted in the presence of a base which does not interfere with the reaction course such as a trialkylamine like triethylamine, sodium or potassium carbonate or bicarbonate. Generally, the base is employed in a 2 to 6 molar proportion to the starting material and, preferably, it is used in an about three-fold molar excess. A preferred base is triethylamine.

The "activated ester" forming reagent is used in a large excess over the $C^{63}$ carboxyacid starting material of formula (II). It is in general used in a 5 to 35 molar proportion and, preferably, it is used in an about 20 to 30 times molar excess. The reaction temperature is between 10° C. and 60° C. and, preferably, between 15° C. and 30° C. As usual, the reaction time depends on the other specific reaction parameters and may generally vary between 3 and 48 hours.

The reaction course may be followed by HPLC or TLC to determine when the reaction may be considered as completed and the procedures to recover the desired intermediate can be started. The "activated ester" intermediate can be directly used in the same reaction medium where it is prepared, however, in general, it is isolated by precipitation with non-solvents or by extraction with solvents and it is used as such, without further purification, in the next reaction step. If desired, however it may be purified by column chromatography such as flash column chromatography or reverse-phase column chromatography.

The obtained "activated ester" intermediate is then reacted with a molar excess of the amine derivative of formula (III) in the presence of an organic polar solvent at a temperature between 5° C. and 60° C., preferably between 10° C. and 30° C.

The organic polar solvent can be in this case a polar protic solvent or an aprotic one.

Preferred examples of organic polar protic solvents are lower($C_2$–$C_4$)alkanols such as, ethanol, n-propanol, isopropanol, n-butanol and the like, or mixtures thereof, preferably used in the dry form.

Preferred examples of organic polar aprotic solvent are N,N-dimethylformamide (DMF), hexamethylphosphoramide (HMPA), or mixtures thereof, 1,3-dimethyl-3,4,5,6-tetrahydro-2(1H)-pyrimidone (DMPU), dimethylsulfoxide (DMSO) or dimethoxyethane (DME).

The reaction of the "activated ester" with the selected amine of formula (III) can be carried out at a temperature between 5° C. and 60° C. but the preferred temperature is generally comprised between 10° C. and 30° C., most preferably between 20° C. and 25° C., while a preferred molar proportion between the "activated ester" intermediate and the amine (III) as above defined is from 1:5 to 1:30, and more preferably from 1:10 to 1:20. The reaction course may be monitored as usual by TLC or HPLC.

In case that the reactant amine is a polyamine of formula (III) one or more of its amino groups which are not involved in the amide bond formation may be conveniently protected. Also in these cases, the suitable protecting groups are those mentioned previously for the N15.

Accordingly, the resulting $N^{63}$-protected amide derivatives are then deprotected under similar conditions as those reported above for the deprotection at the 15-position.

The compounds of formula (I) wherein Y is hydroxymethyl, $R_1$, $R_2$, M, X and Z are as described at the beginning of this description may be prepared by reduction of the corresponding derivatives of formula (I) wherein $R_2$, M, X and Z have the same meaning as above, Y is ($C_1$–$C_4$) alkoxycarbonyl and $R_1$ is a suitable protecting group of the $N^{15}$-amino function, with an alkali metal borohydride, preferably selected from sodium borohydride, potassium borohydride and sodium cyanoborohydride at a temperature comprised between 0° C. and 40° C., in an aqueous or hydroalcoholic medium. The de-protection of the $N^{15}$-amino function may be effected according to the conditions described before.

Use of this method is specifically required for preparing the compounds of formula (I) wherein Y is hydroxymethyl, X is hydroxy, $R_1$, $R_2$ and M are as described at the beginning of this description and Z is hydrogen. In said case the starting material submitted to the reduction step under the conditions described above is a compound of formula (II) wherein Y' is ($C_1$–$C_4$)alkoxycarbonyl , X' is hydroxy, $R'_2$ and M' have the same meanings as $R_2$ and M, respectively, and $R'_1$ is a suitable protecting group of the $N^{15}$-amino function. The specific preparation of said starting compound is disclosed in the International Patent Application No. PCT/EP92/00374 and it is carried out according to the general method for preparing the starting ester of formula (II) described above.

Generally, the hydroalcoholic medium utilized in the reduction rections mentioned above is a mixture of water and a water soluble or partially mixable lower alkanol wherein the ratio water/lower alkanol ranges between 40/60 and 90/10 (v/v), preferably between 60/46 (v/v) and 68/32 v/v, most preferably is 65/35 (v/v).

Although the reaction occurs, in some cases, also in the presence of lower amounts of water, e.g. in mixtures water/lower alkanol 30/70 or 20/80, in general, the reaction rate is very low when the ratio water/lower alkanol is lower than 40/60.

Preferred lower alkanols are linear and branched ($C_1$–$C_4$) alkyl alcohols, among which the most preferred are n-butanol, ethanol and methanol.

Sometimes, in particular cases, a small amount of a polar co-solvent can be added to completely dissolve the starting material during the course of the reaction, e.g. N,N-dimethylformamide, 1,3-dimethyl-3,4,5,6-tetrahydro-2(1H)-pyrimidone (DMPU), dimethylsulfoxide. Sometimes, variable amounts of diethyl ether are also added to avoid foaming.

As alkali metal borohydride the sodium borohydride in the most preferred one. The suitable amount of alkali metal borohydride employed may vary depending on the solvent used and on the temperature of the reaction, but it is advisable to use an amount of alkali metal borohydride in a large excess over the stoichiometric requirement in such a way that the pH of the reaction mixture is neutral or alkaline, preferably between pH 7 and 10. In general the molar ratio between the alkali metal borohydride and the antibiotic starting material is comprised between 50 and 300.

The reaction temperature may vary considerably depending on the specific starting materials and the reaction conditions. In general, it is preferred to conduct the reaction at a temperature between 0° and 40° C., more preferably at room temperature.

Also the reaction time may vary considerably depending on the other reaction parameters, however it has to be carefully controlled. In general the reaction is completed in about 1–4 hours. If the reaction is prolonged for more than 4 hours, undesirable side reactions can occur which can also provoke the cleavage of some peptide bonds of the core of the molecule.

In any case, the reaction course is monitored by TLC or, preferably, by HPLC according to methods known in the art. On the basis of the results of these assays a man skilled in the art will be able to evaluate the reaction course and decide when to stop the reaction and start working up the reaction mass according to known per se techniques which include, for instance, extraction with solvents, precipitation by addition of non-solvents, etc., in conjunction with further separations and purifications by column chromatography, when needed.

After the reaction is completed, the excess of the alkali metal borohydride is eliminated by adding a suitable amount of an acid, for example, a ($C_1$–$C_4$)alkyl organic acid, a ($C_1$–$C_6$)alkyl sulfonic acid, an aryl sulfonic acid and the like, dissolved in a polar protic solvent such as, for example a ($C_1$–$C_4$)alkyl alcohol.

Alternatively, the compounds of formula (I) wherein Y is hydroxymethyl, $R_1$, $R_2$ and M are as described at the beginning of this description, X is an amino rest —$NR_3$—$alk_1$—($NR_4$—$alk_2$)$_p$—($NR_5$—$alk_3$)$_q$—W wherein $R_3$, $R_4$, $R_5$, $alk_1$, $alk_2$, $alk_3$, p, q and W have the same meanings as at the beginning of this description and Z, is hydrogen are prepared by following the same amidation procedure described above by reacting the corresponding compound of formula (I) wherein Y is hydroxymethyl, X is hydroxy, $R_1$, $R_2$ and M have the same meaning as above, and Z is hydrogen with an amine of formula (III) as described above.

Also in this case the amidation reaction can be carried out by using an appropriate condensing agent or through the intermediate formation of an "activated ester" as described above for the preparation of compounds of formula (I) wherein Y is ($C_1$–$C_4$)alkoxycarbonyl.

In general, the amidation of the derivatives of formula (I) wherein Y is hydroxymethyl, X is hydroxy and Z is hydrogen by using PyBOP as the condensing agent produces end compounds of formula (I) wherein Z represent hydrogen even when PyBOP is employed in a large molar excess over the carboxylic acid starting material. When the amidation reaction is carried out via formation of an "activated ester" of the compound of formula (I) wherein X is hydroxy, Y is hydroxymethyl, and Z is hydrogen, it is preferred to have protected the $N^{15}$-amino group of said compound by means of the protecting groups described before.

A further procedure for the preparation of a compound of formula (I) wherein Y is ($C_1$–$C_4$)alkoxycarbonyl or hydroxymethyl, $R_1$, $R_2$, M and Z are as at the beginning of this description, X represents an amino rest

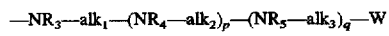

wherein $R_3$, $R_4$, $R_5$, each independently represents hydrogen or ($C_1$–$C_4$)alkyl, $alk_1$, $alk_2$, $alk_3$ and W are as at the beginning of this description, p is 1 and q represents 1 or zero, consists in reacting a $N^{15}$-protected derivative of a $N^{63}$ amide (in this description the term "$N^{63}$" refers to the nigrogen atom of the carboxyamide group involving the carbon atom of the A 40926 molecule identified with the number 63) of formula (I) wherein Y, $R_2$, M and Z are as above and X is an amino rest

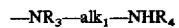

wherein $R_3$, $R_4$ and $alk_1$ are as above or

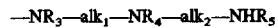

wherein $R_3$, $R_4$, $R_5$, $alk_1$ and $alk_2$ are as above with an amine reactant of the formula (IV) or (IVa) respectively.

wherein the symbols $R_5$, $alk_2$, $alk_3$ and W are as above, q is zero or 1 and r represents halo, methanesulfonyl or tosyl, in the presence of an acid acceptor in an inert solvent.

The $N^{15}$-protected derivative of the $N^{63}$ amide referred above are prepared according to the general method for the preparation of the compounds of formula (I) of this invention. The de-protection of the $N^{15}$-amino function is carried out according to the conditions described before.

Also in the case of the above alkylation method it may be useful or necessary to protect those amino function(s) other than the $N^{15}$-amino group of the $N^{63}$ amide campound of formula (I) and/or of the amine reactant (IV) or (IVa) which are not involved in the alkylation reaction. The resulting $N^{63}$-protected amides can be de-protected according to the conditions described above.

The protecting groups to be utilized in all the above mentioned reactions are those already described above. Particular attention, however, has to be made for what concerns the deprotection step of the derivatives of formula (I) wherein Y is hydroxymethyl. For these compounds, in fact, when the protecting group at the 15-position is removable under acidic conditions, the deprotection step is critical, due to the relatively fast competitive displacement of the respective 56-acylglucosamine moiety, for instance, by treatment with dry trifluoroacetic acid (TFA). Anyway, these undesired side-reactions can be easily minimized. For instance when t-butyloxycarbonyl (t-BOC) is used as protecting group the following conditions can be employed: treatment with dry TFA for one minute at room temperature or for 10 to 30 minutes at 0 °to 5° C., followed by quick precipitation of the reaction product with diethyl ether or a mixture methanol/diethyl ether at 0 °to 5° C. On the contrary, with compounds of formula (I) wherein Y is carboxy or methoxycarbonyl it has been observed that the 56-acylaminoglucuronic acid moiety is markedly more stable to TFA. In fact, the formation of traces of the corresponding de-glucuronyl pseudoaglycones is observed only after 1 hour reaction. However, in these cases, the t-BOC-deprotection is carried out in 30 minutes.

Another suitable method for removing the t-BOC protecting group without substantially affecting the other portions of the molecule consists in a treatment with dry TFA in dichloromethane at 0°–10° C. for 1–2 hours, followed by precipitation of the reaction product by addition of a non-solvent.

The compounds of formula (I) wherein $R_1$, $R_2$, M, X and Z are as at the beginning of this description and Y is carboxy, are prepared from the corresponding compounds of formula (I) wherein Y is ($C_1$–$C_4$)alkoxy-carbonyl, preferably methoxycarbonyl and all other symbols are as above by treatment with aqueous alkali metal hydroxides (e.g. NaOH or KOH) at the temperature between 0° and 30° C. (higher temperatures must be avoided to prevent epimerization at the carbon atom in the position 3 of the molecule), in an organic inert solvent, for instance, a di-(lower alkyl) ether of ehtylene glycol or tetrahydrofuran. The compounds of formula (I) wherein $R_1$, $R_2$, M, X and Z are as at the beginning of this description and Y is aminocarbonyl, ($C_1$–$C_4$) alkylaminocarbonyl, di($C_1$–$C_4$)alkylaminocarbonyl wherein the alkyl moiety may bear a substituent selected from hydroxy, amino, ($C_1$–$C_4$)alkylamino and di($C_1$–$C_4$) alkylamino may be prepared according to the following procedures:

i) Preparation of derivatives wherein the symbol Y and the moiety COX of $C^{63}$ represent the same group ($C_1$–C4) alkylaminocarbonyl or di($C_1$–$C_4$)alkyl-aminocarbonyl wherein the alkyl moiety may bear a substituent selected from amino, ($C_1$–C4)alkylamino and di($C_1$–$C_4$)alkylamino:

(a) Amidation of antibiotic A 40926 complex, its de-mannosyl derivative or a factor thereof (formula (II), X'=hydroxy, Y'=carboxy, R'$_1$, R'$_2$ and M' the same as $R_1$, $R_2$ and M above) with a large excess of the appropriate amine of formula (III) wherein the symbols $R_3$, $R_4$, $R_5$, $alk_1$, $alk_2$, $alk_3$, p, q and W have the meanings consistent with the above defined carboxyamide rests Y and COX. This amidation reaction is carried out under the same conditions described above.

ii) Preparation of derivatives wherein the symbol Y and the moiety COX of $C_{63}$ represent different carboxamide rests, the meaning of Y being selected from aminocarbonyl, ($C_1$–$C_4$)alkylaminocarbonyl, di($C_1$–$C_4$)alkylaminocarbonyl wherein the alkyl moitety may bear a substituent selected from hydroxy, amino, ($C_1$–$C_4$)alkylamino and di($C_1$–$C_4$)alkylamino and the meaning of X being an amino rest as defined at the beginning of this description:

Method A: Amidation of the corresponding compound of formula (I) wherein $R_1$, $R_2$, M and Z are as at the beginning of this description, X represents an amino rest of formula

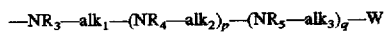

wherein all symbols have the same meanings as at the beginning of this description and Y is carboxy, by reaction with the appropriate amine to form the above defined carboxamide rest Y in the presence of a condesing agent (e.g. PyBOP or DPPA) under the same condition described before;

Method B: (a) protecting the same starting compound of Method A on the $N^{15}$-amino function (e.g. with a t-BOC or CBz group); (b) forming an "activated ester" of the carboxy group at position $6^B$ (e.g. by reaction with chloroacetonitrile); (c) reacting the "activated ester" moiety of said compound with the appropriate amine to form the above defined carboxyamide rest Y under the same conditions described before; (d) optionally removing the $N^{15}$-protecting group by the methods described above (e.g. by acidolysis or hydrogenolysis).

The compounds of formula (I) wherein M is hydrogen are currently prepared according to the procedures described above by using the corresponding starting molecule of formula (II) wherein M' is hydrogen.

In addition, an alternative procedure for the preparation of a compound of formula (I) wherein M is hydrogen consists in the transformation of a compound of formula (I) wherein M is α-D-mannopyranosyl or 6-0-acetyl-α-D-mannopyranosyl into the corresponding compound wherein M is hydrogen by means of selective acid hydrolysis according to the conditions described in EP-A 240609.

As described above, the compounds of formula (I) may consists of unitary compounds corresponding to the individual factors of the precursor antibiotic A 40926 or of mixtures thereof, in any proportion. Since, in most cases, the biological activity of the mixtures is very similar to that of the individual factors, there is no specific interest to separate the individual components when a mixture is obtained. However, when pure factors of formula (I) are desired, they can be individually separated from their mixtures by means of reverse phase column chromatography according to the method described in EP 177882. Alternatively, they may be prepared by using unitary starting materials of formula (II) corresponding to the individual factors of the antibiotic A 40926 complex.

Under the general methods and conditions described here it may be useful to utilize a precursor A 40926 complex which contains one of the individual factors, (e.g. factor $B_0$) in a preponderant proportion with respect to the reamining components of the mixture (e.g. 60% by HPLC). Accordingly, the compounds of formula (I) resulting from such precursor through the process of this invention, when are not specifically submitted to the above mentioned separation procedure, generally consist of mixtures wherein the preponderant component corresponds to the same factor whose ratio is predominant in said A 40926 complex precursor.

A method for preparing an A-40926 complex enriched in its factors A and/or $B_0$ or PA and/or PB is described, for instance, in EP-A-259781.

The compounds of this invention possess basic functions which can form salts with organic and inorganic acids according to conventional procedures.

Representative and suitable acid addition salts of the compounds of the present invention include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric , glutaric, glycolic, phthalic, tartaric, lauric, stearic, salicylic, methanesulfonic, benzenesulfonic, sorbic, picric, benizoic, cinnamic, and the like acids.

The compounds of formula (I) wherein X is hydroxy and Y is hydroxymethyl and the compounds wherein Y is carboxy possess also an acid function which can form salts with organic and inorganic bases.

Representative examples of the bases that can form salts with the compounds of the present invention possessing an acid function are: alkali metal or alkaline-earth-metal hydroxides such as sodium, potassium, calcium, magnesium, barium hydroxide, ammonia and aliphatic, alicyclic or aromatic organic amines such as methylamine, dimethylamine, triethylamine, ethanolamine and picoline.

The transformation of the "non-salt" compounds of the invention into the corresponding addition salts, and the reverse, i.e. the transformation of an addition salt of a compound of the invention into the non-salt form, are within the ordinary technical skill and are encompassed by the present invention.

For instance, a compound of formula (I) can be transformed into the corresponding salts with acids or bases by dissolving or suspending the non-salt form in an aqueous solvent and adding a slight molar excess of the selected acid or base. The resulting solution or suspension is then lyophilized to recover the desired salt.

In case the final salt is insoluble in a solvent where the non-salt form is soluble, the salt may be recovered by filtration from the solution of the non-salt form after adding the stoichiometric amount or a slight molar excess of the selected acid or base.

The non-salt form can be prepared from a corresponding salt dissolved in an aqueous solvent which is then neutralized to free the non-salt form. This is then recovered for instance by extraction with an organic solvent or is transformed into another addition salt by adding the selected acid or base and working up as above.

When following the neutralization, desalting is necessary, a common desalting procedure may be employed. For example, column chromatography on controlled pore polydextrane resins (such as SEPHADEX LH 20) or silanized silica gel may be conveniently used. After eluting the undesired salts with an aqueous solution, the desired product is eluted by means of linear gradient or step-gradient of a mixture of water and a polar or apolar organic solvent, such as acetonitrile/water from 50:50 to about 100% acetonitrile.

As it is known in the art, the salt formation either with pharmaceutically acceptable acids and bases or non-pharmaceutically acceptable acids and bases may be used as a convenient purification technique. After formation and isolation, the salt form of a compound of formula (I) can be transformed into the corresponding non-salt or into a pharmaceutically acceptable salt.

However,in view of the similarity of the properties of the compounds of formula I and their salts, what is said in the present application when dealing with the biological activities of the compounds of formula (I) applies also to their pharmaceutically acceptable salts.

The following Table I shows a series of representative compounds illustrative of this invention.

TABLE I

| Compound No. | Identification code | $R_1$ | $R_2$ | M | Y | X | Z |
|---|---|---|---|---|---|---|---|
| 1 | RA | H | ($C_9$–$C_{12}$) | α-DMP | $CH_2OH$ | OH | H |
| 2 | MA-A-1/$B_0$ | H | $iC_{10}$ | α-DMP | $COOCH_3$ | $NH(CH_2)_3N(CH_3)_2$ | H |
| 3 | RA-A-1/$B_0$ | H | $iC_{10}$ | α-DMP | $CH_2OH$ | $NH(CH_2)_3N(CH_3)_2$ | H |
| 4 | MA-A-2/$B_0$ | H | $iC_{10}$ | α-DMP | $COOCH_3$ | $NH-(CH_2)_3-[NH(CH_2)_3]_2-NH_2$ | H |
| 5 | MA-A-3/$B_0$ | H | $iC_{10}$ | α-DMP | $COOCH_3$ | $NH(CH_2)_3-N[(CH_2)_3NH_2]_2$ | H |
| 6 | MA-A-1 | H | ($C_9$–$C_{12}$) | α-DMP | $COOCH_3$ | $NH(CH_2)_3N(CH_3)_2$ | H |
| 7 | PyMA-A-1 | H | ($C_9$–$C_{12}$) | α-DMP | $COOCH_3$ | $NH(CH_2)_3N(CH_3)_2$ | $P^\oplus(NC_4H_8)_3$ $CH_3COO^\ominus$ |
| 8 | RA-A-1 | H | ($C_9$–$C_{12}$) | α-DMP | $CH_2OH$ | $NH(CH_2)_3N(CH_3)_2$ | H |
| 9 | RA-A-2 | H | ($C_9$–$C_{12}$) | α-DMP | $CH_2OH$ | $NH(CH_2)_3-[NH(CH_2)_3]_2-NH_2$ | H |
| 10 | RA-A-3 | H | ($C_9$–$C_{12}$) | α-DMP | $CH_2OH$ | $NH-(CH_2)_3-N[(CH_2)_3NH_2]_2$ | H |
| 11 | A-A-1 | H | ($C_9$–$C_{12}$) | α-DMP | COOH | $NH(CH_2)_3N(CH_3)_2$ | H |
| 12 | PyA-A-1 | H | ($C_9$–$C_{12}$) | α-DMP | $COO^\ominus$ | $NH(CH_2)_3N(CH_3)_2$ | $P^\oplus(NC_4H_8)_3$ |
| 13 | A-A-3/$B_0$ | H | $iC_{10}$ | α-DMP | COOH | $NH(CH_2)_3-N[(CH_2)_3NH_2]_2$ | H |
| 14 | ABA-A-1 | H | ($C_9$–$C_{12}$) | α-DMP | $CONHCH_3$ | $NH(CH_2)_3N(CH_3)_2$ | H |
| 15 | ADA-A-1 | H | ($C_9$–$C_{12}$) | α-DMP | $CONH(CH_2)_3N(CH_3)_2$ | $NH(CH_2)_3N(CH_3)_2$ | H |
| 16 | PyRA-A-1 | H | ($C_9$–$C_{12}$) | α-DMP | $CH_2OH$ | $NH(CH_2)_3N(CH_3)_2$ | $P^\oplus(NC_4H_8)_3$ $CH_3COO^\ominus$ |
| 17 | A-A-2 | H | ($C_9$–$C_{12}$) | α-DMP | COOH | $NH-(CH_2)_3-[NH(CH_2)_3]_2-NH_2$ | H |
| 18 | AA-A-1 | H | ($C_9$–$C_{12}$) | α-DMP | $CONH_2$ | $NH(CH_2)_3N(CH_3)_2$ | H |
| 19 | ACA-A-1 | H | ($C_9$–$C_{12}$) | α-DMP | $CON(CH_3)_2$ | $NH(CH_2)_3N(CH_3)_2$ | H |
| 20 | AA-A-2/$B_0$ | H | $iC_{10}$ | α-DMP | $CONH_2$ | $NH-(CH_2)_3-[NH(CH_2)_3]_2-NH_2$ | H |
| 21 | AA-A-3 | H | ($C_9$–$C_{12}$) | α-DMP | $CONH_2$ | $NH(CH_2)_3-N[(CH_2)_3NH_2]_2$ | H |
| 22 | PyA-A-3 | H | ($C_9$–$C_{12}$) | α-DMP | COOH | $NH(CH_2)_3-N[(CH_2)_3NH_2]_2$ | $P^\oplus(NC_4H_8)_3$ $Cl^\ominus$ |
| 23 | PyAA-A-1 | H | ($C_9$–$C_{12}$) | α-DMP | $CONH_2$ | $NH(CH_2)_3N(CH_3)_2$ | $P^\oplus(NC_4H_8)_3$ $Cl^\ominus$ |
| 24 | RA-A-4 | H | ($C_9$–$C_{12}$) | α-DMP | $CH_2OH$ | 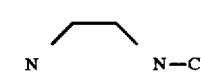 N-methylpiperazinyl | H |
| 25 | MA-A-4 | H | ($C_9$–$C_{12}$) | α-DMP | $COOCH_3$ | 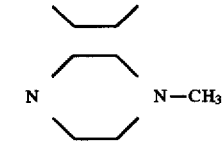 N-methylpiperazinyl | H |

TABLE I-continued

| Compound No. | Identification code | $R_1$ | $R_2$ | M | Y | X | Z |
|---|---|---|---|---|---|---|---|
| 26 | DM-RA-A-1 | H | $(C_9-C_{12})$ | H | $CH_2OH$ | $NH(CH_2)_3N(CH_3)_2$ | H |
| 27 | DM-RA-A-1/$B_0$ | H | $iC_{10}$ | H | $CH_2OH$ | $NH(CH_2)_3N(CH_3)_2$ | H |
| 28 | DM-MA-A-1 | H | $(C_9-C_{12})$ | H | $COOCH_3$ | $NH(CH_2)_3N(CH_3)_2$ | H |
| 29 | RA-A-1/B | H | $iC_{10}/nC_{11}$ | α-DMP | $CH_2OH$ | $NH(CH_2)_3N(CH_3)_2$ | H |
| 30 | MA-A-1/B | H | $iC_{10}/nC_{11}$ | α-DMP | $COOCH_3$ | $NH(CH_2)_3N(CH_3)_2$ | H |
| 31 | RA-A-1/A | H | $nC_{10}$ | α-DMP | $CH_2OH$ | $NH(CH_2)_3N(CH_3)_2$ | H |
| 32 | MA-A-1/A | H | $nC_{10}$ | α-DMP | $COOCH_3$ | $NH(CH_2)_3N(CH_3)_2$ | H |
| 33 | RA-A-1/$B_1$ | H | $nC_{11}$ | α-DMP | $CH_2OH$ | $NH(CH_2)_3N(CH_3)_2$ | H |
| 34 | MA-A-1/$B_1$ | H | $nC_{11}$ | α-DMP | $COOCH_3$ | $NH(CH_2)_3N(CH_3)_2$ | H |

$(NC_4H_8)_3$ = (pyrrolidino)$_3$
α-DMP = α-D-mannopyranosyl
$iC_{10}$ = 9-methyldecyl (corresponding to factor $B_0$ of A 40926)
$nC_{10}$ = n-decyl (corresponding to factor A of A 40926)
$nC_{11}$ = n-undecyl (corresponding to factor $B_1$ of A 40926)
$iC_{10}/nC_{11}$ = 9-methyldecyl and n-undecyl (corresponding to factor B of A 40926)
$(C_9-C_{12})$ = $C_9-C_{12}$ alkyl (corresponding to all factors of A 40926 complex)

The antibiotic A 40926 derivatives of the present invention are mainly active against Gram-positive bacteria.

In particular, the compounds of the present invention show a surprising activity against glycopeptide resistant Enterococci and Staphylococci.

The antimicrobial activity, expressed as minimal inhibitory concentration (MIC), of the antibiotic A 40926 derivatives of formula (I), against selected strains of Gram-positive bacteria was determined in comparison with teicoplanin and with antibiotic A 40926 complex. The microbroth dilution method in Müller-Hinton medium broth in the presence of 0.01 percent (w/v) of bovine albumin serum (fraction V Sigma) was used. Final inoculum was about $10^5$ cfu/ml and MIC was read as the lowest concentration (mcg/ml) which showed no visible growth after 18–24 hours incubation at 37° C.

The following Table II show the antimicrobail spectrum of a series of compounds representative of the invention.

TABLE II

| | | MIC (mcg/ml) | | | | | |
|---|---|---|---|---|---|---|---|
| L No.[1] | Organism Strain | TEICO-PLANIN* | A/40926 complex* | Compound 1 RA | Compound 2 MA-A-1/$B_0$ | Compound 3 RA-A-1/$B_0$ | Compound 4 MA-A-2/$B_0$ |
| 165 | Staph. aureus | 0.25 | 0.13 | 0.13 | 0.13 | 0.13 | 0.25 |
| 561 | Staph. aureus | 8 | 8 | 4 | 1 | 0.13 | 0.5 |
| 147 | Staph. epidermidis | 4 | 4 | 4 | 0.25 | 0.13 | 0.13 |
| 533 | Staph. epidermidis | 8 | 8 | 4 | 0.13 | 0.06 | 0.25 |
| 602 | Staph. haemolyticus | 32 | 16 | 8 | 0.5 | 0.13 | 0.25 |
| 49 | Strep. pyogenes | 0.13 | 0.13 | 0.13 | 0.13 | 0.06 | 0.13 |
| 44 | Strep. pneumoniae | 0.06 | 0.06 | 0.03 | 0.03 | 0.01 | 0.13 |
| 149 | Entero. faecalis | 0.13 | 0.13 | 0.13 | 0.13 | 0.06 | 0.25 |
| 562 | Entero. faecalis | >128 | 64 | 16 | 8 | 8 | 16 |
| 997 | Neisseria gonorrh. | 32 | 0.13 | 2 | 8 | 16 | 32 |
| 47 | Esch. coli | >128 | >128 | 128 | >128 | >128 | >128 |
| 4 | Pseudomonas aerug. | >128 | 128 | >128 | 128 | 128 | 64 |
| 79 | Proteus vulgaris | >128 | 64 | >128 | 32 | 128 | 64 |
| L No.[1] | Organism Strain | Compound 5 MA-A-3/$B_0$ | Compound 6 MA-A-1 | Compound 7 PyMA-A-1 | Compound 8 RA-A-1 | Compound 9 RA-A-2 | Compound 10 RA-A-3 |
| 165 | Staph. aureus | 0.06 | 0.13 | 1 | 0.13 | 0.06 | 0.06 |
| 561 | Staph. aureus | 0.5 | 1 | 16 | 0.13 | 0.25 | 0.13 |
| 147 | Staph. epidermidis | 0.13 | 0.25 | 8 | 0.13 | 0.13 | 0.06 |
| 533 | Staph. epidermidis | 0.13 | 0.13 | 4 | 0.06 | 0.25 | 0.06 |
| 602 | Staph. haemolyticus | 0.06 | 0.5 | 8 | 0.13 | 0.13 | 0.13 |
| 49 | Strep. pyogenes | 0.03 | 0.13 | 0.13 | 0.06 | 0.06 | 0.03 |
| 44 | Strep. pneumoniae | 0.03 | 0.03 | 0.06 | 0.01 | 0.06 | 0.01 |
| 149 | Entero. faecalis | 0.13 | 0.13 | 0.5 | 0.13 | 0.13 | 0.13 |
| 562 | Entero. faecalis | 8 | 8 | 8 | 8 | 8 | 8 |
| 997 | Neisseria gonorrh. | 32 | 8 | >128 | 16 | 64 | 32 |
| 47 | Esch. coli | >128 | >128 | >128 | >128 | >128 | >128 |
| 4 | Pseudomonas aerug. | 64 | 128 | >128 | 128 | 64 | 16 |
| 79 | Proteus vulgaris | 64 | 32 | >128 | >128 | >128 | >128 |
| L No.[1] | Organism Strain | Compound 11 A-A-1 | Compound 12 PyA-A-1 | Compound 13 A-A-3/$B_0$ | Compound 14 ABA-A-1 | Compound 15 ADA-A-1 | |
| 165 | Staph. aureus | 0.13 | 0.25 | 0.06 | 0.13 | 0.13 | |

TABLE II-continued

| | | | MIC (mcg/ml) | | | |
|---|---|---|---|---|---|---|
| 561 | Staph. aureus | 0.5 | 4 | 0.13 | 16 | 1 |
| 147 | Staph. epidermidis | 0.25 | 2 | 0.13 | 8 | 0.13 |
| 533 | Staph. epidermidis | 0.13 | 1 | 0.06 | 32 | 0.13 |
| 602 | Staph. haemolyticus | 0.13 | 2 | 0.06 | 16 | 0.25 |
| 49 | Strep. pyogenes | 0.03 | 0.06 | 0.03 | 0.06 | 0.06 |
| 44 | Strep. pneumoniae | 0.06 | 0.06 | 0.03 | 0.01 | 0.06 |
| 149 | Entero. faecalis | 0.13 | 0.5 | 0.13 | 0.13 | 0.06 |
| 562 | Entero. faecalis | 16 | 4 | 16 | 8 | 8 |
| 997 | Neisseria gonorrh. | 1 | 128 | 8 | >128 | 16 |
| 47 | Esch. coli | >128 | >128 | >128 | >128 | >128 |
| 4 | Pseudomonas aerug. | >128 | >128 | >128 | >128 | >128 |
| 79 | Proteus vulgaris | >128 | >128 | >128 | >128 | >128 |

| L No.[1] | Organism Strain | Compound 16 PyRA-A-1 | Compound 24 RA-A-4 | Compound 25 MA-A-4 |
|---|---|---|---|---|
| 165 | Staph. aureus | 1 | 0.06 | 0.13 |
| 561 | Staph. aureus | 16 | 2 | 4 |
| 147 | Staph. epidermidis | 4 | 0.25 | 1 |
| 533 | Staph. epidermidis | 4 | 0.13 | 2 |
| 602 | Staph. haemolyticus | 8 | 0.5 | 2 |
| 49 | Strep. pyogenes | 0.06 | 0.03 | 0.06 |
| 44 | Strep. pneumoniae | 0.06 | 0.03 | 0.06 |
| 149 | Entero. faecalis | 1 | 0.06 | 0.13 |
| 562 | Entero. faecalis | 8 | 8 | 8 |
| 997 | Neisseria gonorrh. | >128 | 16 | 16 |
| 47 | Esch. coli | >128 | >128 | >128 |
| 4 | Pseudomonas aerug. | >128 | >128 | >128 |
| 79 | Proteus vulgaris | >128 | >128 | >128 |

[1]Code number of the strains of the internal collection
*Comparison compound

The following Table III shows in vitro activity data of some representative compounds of this invention in comparison with teicoplanin and vancomycin regarding the in vitro activity against Enterococcal strains highly resistant to glycopeptides in common therapy.

The following Table IV shows the results of some representative compounds of this invention in experimental streptococcal septicemia in mice.

The experiments have been carried out according to the procedure described by V. Arioli et al., Journal of Antibiotics 29, 511 (1976).

TABLE III

| | MIC (µg/ml) | | | |
|---|---|---|---|---|
| Organism Strain[1] | COMPOUND 6 MA-A-1 | COMPOUND 8 RA-A-1 | TEICOPLANIN | VANCOMYCIN |
| *Enterococcus faecalis* | | | | |
| L 560 | 32 | 32 | >128 | >128 |
| L 562 | 8 | 8 | >128 | >128 |
| L 563 | 16 | 16 | >128 | >128 |
| *Enterococcus faecium* | | | | |
| L 564 | 8 | 8 | >128 | >128 |
| L 565 | 8 | 8 | >128 | >128 |
| L 569 | 16 | 16 | >128 | >128 |
| L 1650 | 64 | 32 | >128 | >128 |
| L 1652 | 8 | 8 | >128 | >128 |
| L 1666 | 32 | 32 | >128 | >128 |
| L 1680 | 8 | 8 | >128 | >128 |
| L 1681 | 8 | 8 | >128 | >128 |
| L 1683 | 4 | 8 | >128 | >128 |
| L 1686 | 4 | 4 | >128 | >128 |

[1]internal code numbers

TABLE IV

| COMPOUND NO. | Infecting Organism Strep. pyogenes C 203 Adm. route ($ED_{50}$) sc (mg/kg) |
|---|---|
| Teicoplanin | 0.16 |
| A 40926 complex | 0.35 |
| Compound 1 RA | 0.08 |
| Compound 2 MA-A-1/$B_0$ | 0.03 |
| Compound 3 RA-A-A/$B_0$ | 0.03 |
| Compound 4 MA-A-2/$B_0$ | 0.13 |
| Compound 5 MA-A-3/$B_0$ | 0.04 |
| Compound 6 MA-A-1 | 0.03 |
| Compound 7 PyMA-A-1 | 0.11 |
| Compound 8 RA-A-1 | 0.03 |
| Compound 11 A-A-1 | 0.03 |
| Compound 12 PyA-A-1 | 0.04 |
| Compound 13 A-A-3/$B_0$ | 0.05 |
| Compound 15 ADA-A-1 | 0.05 |
| Compound 16 PyRA-A-1 | 0.06 |

The data represented above show that, although generally less active against *Neisseria gonorrhoeae* than the percursor A 40926, the compounds of this invention have better activity against clinical isolates of Staphylococci and Enterococci, if compared with the reference compounds. In particular, they are:

a) markedly more active in vitro than teicoplanin and A 40926 against glycopeptide-intermediate or -resistant staphylococci, in particular coagulase-negative and methicillin-resistant staphylococci;

b) active in vitro against highly glycopeptide-resistant enterococci, which are highly resistant to teicoplanin and vancomycin and somewhat resistant to A-40926 (MIC>64 mcg/ml);

c) more effective in vivo than teicoplanin and A 40926 in the streptococcal septicemia in mice.

In view of the above reported antimicrobial activity, the compounds of the present invention can effectively be employed as the active ingredients of the antimicrobial preparations used in human and veterinary medicine for the prevention and treatment of infectious diseases caused by pathogenic bacteria which are susceptible to said active ingredients, in particular, for the treatment of infections caused by Enterococci, Streptococci and Staplylococci strains which show low sensitivity to glycopeptide antibiotics.

The compounds of the present invention can be administered orally, topically or parenterally, the parenteral administration route being preferred.

Depending on the route of administration, these compounds can be formulated into various dosage forms. Preparations for oral administration may be in the form of capsules, tablets, liquid solutions or suspensions. As known in the art, the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidone, gelatin, sorbitol, tragacanth, acacia, flavoring agents, and acceptable disintegrating and wetting agents. The liquid preparations, generally in the form of aqueous or oily solutions or suspensions, may contain conventional additives such as suspending agents.

For topical use the compounds of the present invention may also be prepared in suitable forms for absorption through the mucous membranes of the nose and throat or bronchial tissues and may conveniently take the form of liquid sprays or inhalants, lozenges, or throat paints.

For medication of the eyes or ears, the preparation may be presented in liquid or semi-liquid form. Topical applications may be formulated in hydrophobic or hydrophilic bases as ointments, creams, lotions, paints, or powders.

For rectal administration the compounds of the invention are administered in the form of suppositories admixed with conventional vehicles, such as, for example, cocoa butter, wax, spermaceti or polyethylenglycols and their derivatives.

Compositions for injection may take such forms as suspensions, solutions, or emulsions in oily or aqueous vehicles, and may contain formulatory agents such as suspending, stabilizing and/or dispersing agents.

Alternatively, the active ingredient may be in powder form for reconstitution at the time of delivery with a suitable vehicle, such as sterile water.

The amount of active principle to be administered depends on various factors such as the size and conditions of the subject to be treated, the route and frequency of administration, and the causative agent involved.

The compounds of the invention are generally effective at a dosage comprised between about 1 and about 40 mg of active ingredient per Kg of body weight. Depending on the characteristics of the specific compound, the infection and the patients, the effective dose can be administered in a single administration per day or divided in 2 to 4 administrations per day. Particularly desirable compositions are those prepared in the form of dosage units containing from about 30 to about 500 mg per unit.

EXAMPLE 1

Preparation of the starting material (MA) (Compound of formula (II) wherein Y' is —$COOCH_3$, X' is —OH, $R'_1$ is —H, $R'_2$ is ($C_9$–$C_{12}$)alkyl corresponding to the factors of A 40926 complex, M' is α-D-mannopyranosyl and Z is —H)

Antibiotic A 40926 complex (150 mg; 0.0866 mmole), obtained according to EP-A-177882, is dissolved in methanol (30 ml) and the pH adjusted to 2 with concentrated sulfuric acid. The mixture is stirred at room temperature for 26 hours. A precipitate appears when the pH is brought to 6 with 0.15 ml of triethylamine (TEA). After addition of diethyl ether the precipitate is collected, washed thoroughly with diethyl ether and dried. Yield: 150 mg (99%).

EXAMPLE 2

Preparation of compound 1 (RA) (Compound of formula (I) wherein Y is —$CH_2OH$, X is —OH, $R_1$ is —H, $R_2$ is ($C_9$–$C_{12}$)alkyl corresponding to the factors of A 40926 complex, M is α-D-mannopyranosyl and Z is —H)

Step a: preparation of $N^{15}$-(t-BoC)-MA

To a stirred solution of 1.8 g of the compound prepared according to Example 1 (MA) and 1 g of sodium bicarbonate in 50 ml of a dioxane/water 1/1 solution, a solution of 0.25 g of di-tert-butyl-dicarbonate in 5 ml of dioxane is added at 5° C. dropwise within 15 minutes. After 1 hour at room temperature, the reaction mixture is adjusted at pH 4 with 1N HCl. Afterwards, 150 ml of water are added and the resulting mixture is extracted with n-butanol (2×100 ml). The organic layer is separated, washed with 100 ml of water and then it is concentrated to a small volume(about 25 ml) at 40° C. under reduced pressure. The solid precipitated by adding diethyl ether (100 ml) is collected and dried in vacuo at room temperature overnight to yield 1.6 g of the title compound $N^{15}$-(t-BOC)-MA enough pure for the next step.

Step b: preparation of $N^{15}$-(t-BOC)-RA

To a stirred suspension of 0.9 g of the compound prepared according to the step a above in 50ml of water, 30 ml of a n-butanol/diethyl ether 1/1 mixture are added followed by 0.9 g of sodium borohydride. The reducing agent is added portionwise in 30 minutes at room temperature, then the reaction mixture is stirred at room temperature for 1 hour. Afterwards, it is cooled at 5° C. and 1.5 ml of glacial acetic acid are added followed by 50 ml of water. The resulting mixture is extracted with n-butanol (100 ml) and the organic layer is worked up as described above to give 0.8 g of the title compound $N^{15}$-(t-BOC)-RA enough pure for the final step c.

Step c: A solution of 0.5 g of the compound $N^{15}$-(t-BOC)-RA prepared according to the step b above in 5 ml of dry trifluoroacetic acid (TFA) is stirred at room temperature for 1 minute (or altrnatively at 0°–5° C. for 20–30 minutes) and then it is poured in 10 ml of a methanol/diethyl ether ¼ mixture at 0°–5° C. The title compound RA is collected by filtration to yield, after washing with diethyl ether and drying at room temperature in vacuo overnight, 0.35 g of product. A 0.15 g pure sample of compound RA is prepared by reverse-phase column chromatography on silanized silica gel by combining all fractions containing the pure individual factors, as described here below.

EXAMPLE 3

Preparation of compound 2 (MA-A-1/$B_0$) and 6 (MA-A-1) (Compound of formula (I) wherein Y is —COOCE$_3$, X is —NH—(CH$_2$)$_3$—N(CH$_3$)$_2$, $R_1$ is —H, $R_2$ is 9-methyldecyl (MA-A-1/$B_0$) or (C$_9$–C$_{12}$)alkyl corresponding to the factors of A 40926 complex (MA-A-1), M is α-D-mannopyranosyl and Z is —H)

Method A

Step a: preparation of $N^{15}$-(t-BOC)-MA-A-1

To a stirred solution of 1.3 g of $N^{15}$-(t-BOC)-MA in 30 ml of DMSO (prepared according to step a of Example 2 above), 0.2 ml of 3,3-dimethylamino-1-propylamine and 0.3 ml of diphenylphosphoroazidate (DPPA) are added. After 4 hours stirring at room temperature, another amount of 0.15 ml of DPPA is added and stirring is continued at room temperature for additional 20 hours. The solid precipitated by adding 170 ml of diethyl ether is collected to give 1.3 g of the title compound $N^{15}$-(t-BOC)-MA-A-1.

Step b: The above product is dissolved in 10 ml of TFA. The resulting solution is stirred at room temperature for 20 minutes and then 90 ml of diethyl ether are added. The precipitated solid is collected, washed twice with 50 ml of diethyl ether, and then it is dried at room temperature in vacuo overnight, yielding 0.9 g of crude title compound (MA-A-1) which is reverse-phase chromatographed on a column of silanized silicagel (by combining only the fractions containing the pure desired individual factor) to give 0.15 g of pure MA-A-1/$B_0$.

Method B

To a stirred solution of 1.8 g (about 1 mmol) of the compound of Example 1 (MA) in 30 ml of DMF, 0.14 ml (about 1.15 mmol) of 3,3-dimethylamino-1-propylamine and 600 mg (about 1.2 mol) of PyBOP are added at room temperature. After stirring at 20°–25° C. for 3 hours, 150 ml of diethyl ether are added. The precipitated solid is collected and then purified by reverse-phase column chromatography (by combining all fractions containing the pure individual factors) yielding 1.15 g of compound MA-A-1.

EXAMPLE 4

Preparation of compound 7 (PyMA-A-1) (Compound of formula (I) wherein Y is —COOCE$_3$, X is —NH—(CH$_2$)$_3$—N(CH$_3$)$_2$, $R_1$ is —H, $R_2$ is (C$_9$–C$_{12}$)alkyl corresponding to the factors of A 40926 complex, M is α-D-mannopyranosyl and Z is P$^{\oplus}$(NC$_4$H$_3$)$_3$ CH$_3$COO$^{\ominus}$)

To a stirred solution of 1.8 g (about 2 mmol) of compound MA prepared as in Example 1 in 40 ml of DMF, 2 ml (about 16 mmol) of 3,3-dimethylamino-1-propylamine and 3.12 g (about 6 mmol) of PyBOP are added at room temperature. After 30 minutes, the reaction mixture is worked-up as described under Example 3, Method B, yielding 1.5 g of the title compound PyMA-A-1.

EXAMPLE 5

Preparation of compound 3 (RA-A-1/$B_0$) and 8 (RA-A-1) (Compound of formula (I) wherein Y is —CH$_2$OH, X is —NH—(CH$_2$)$_3$—N(CH$_3$)$_2$, $R_1$ is —H, $R_2$ is 9-methyldecyl (RA-A-1/$B_0$) or (C$_9$–C$_{12}$)alkyl corresponding to the factors of A 40926 complex (RA-A-1), M is α-D-mannopyranosyl and Z is —H)

Method A

Step a: preparation of $N^{15}$-(t-BOC)-RA-A-1

By substantially following the same procedure as that described in Example 3, Method A, step a, from 2 g of $N^{15}$-(t-BOC)-RA (Example 2, step b) 1.7 g of the title compound $^{15}$-(t-BOC)-RA-A-1 is obtained.

Step b: By substantially following the same procedure as that described in Example 2, step c, from 1.7 g of the above compound $N^{15}$-(t-BOC)-RA-1, 0.22 g of pure compound RA-A-1 is obtained.

The factor RA-A-1/$B_0$ is obtained by operating in the same way as described above with the only difference that in the reverse-phase chromatography purifiation only those fractions which contain the pure desired individual factor are combined.

Method B

To a stirred solution of 50 g (about 27 mmol) of the compound of Example 2 (RA) in 200 ml of DMF, 11 ml (about 90 mmol) of 3,3-dimethylamino-1-propylamine and 18g (about 35 mmol) of PyBOP are added at room temperature. After 15 minutes stirring, 1 liter of ethyl acetate is added and the precipitated solid (about 63 g) is collected and purified by reverse-phase column chromatography (by combining all factions containing the pure individual factors), yielding 25 g of compound RA-A-1

EXAMPLE 6

Preparation of compound 4 (MA-A-2/$B_0$) (Compound of formula (I) wherein Y is —COOCH$_3$, X is —NH—(CH$_2$)$_3$—[NH—(CH$_2$)$_3$—]$_2$—NH$_2$, $R_1$ is —H, $R_2$ is 9-methyldecyl, M is α-D-mannopyranosyl and Z is —H)

Step a: Preparation of $N^{15}$-(t-BOC)-MA, cyanomethyl ester

A solution of 2.5 g of the compound of Example 2, step a ($N^{15}$-(t-BOC)-MA), 0.25 ml of TEA, and 2.5 ml of chloroacetonitrile in 10 ml of dimethylsulfoxide (DMSO) are stirred at room temperature for 4 hours. Afterwards, 90 ml of ethyl acetate are added and the precipitated solid is collected, yielding 2.8 g of crude title compound $N^{15}$-(t-BOC)-MA cyanomethyl ester.

Step b: preparation of $N^{15}$-(t-BOC)-MA-A-2

The above crude cyanomethyl ester compound is dissolved in 30 ml of DMSO. To the resulting solution, 2.8 ml of N,N'-bis-(3-aminopropyl)-1,3-propanediamine are added and the reaction mixture is stirred at room temperature for 4 hours. Afterwards, 200 ml of ethyl acetate are added and the precipitated solid is collected, yielding 3 g of crude title compound $N^{15}$-(t-BOC)-MA-A-2.

Step c: The above crude compound is treated with TFA as described above in Example 3, Method A, step b, to give, after reverse-phase column chromatography (by combining only the fractions containing the pure desired individual factor), 0.45 g of pure compound MA-A-2/B$_0$.

EXAMPLE 7

Preparation of compound 5 (MA-A-3/B$_0$) (Compound of formula (I) wherein Y is —COOH$_3$, X is —NH—(CH$_2$)$_3$—N[—(CH$_2$)$_3$—NH$_2$]$_2$, R$_1$ is —H, R$_2$ is 9-methyldecyl, M is α-D-mannopyranosyl and Z is —H)

Step a: Preparation of N',N"-di(t-BOC)-tris(3-aminopropyl)amine

The N',N"-protected polyamine is prepared as described in International Application Publ. No. WO 90/11300

Step b: Condensation of MA with N',N"-di(t-BOC)-tris(3-aminopropyl)amine

A solution of 18 g (about 10 mmol) of the compound of Example 1 (MA), 14 g (about 36 mmol) of the protected amine, 3 ml (about 22 mmol) of TEA, and 6 ml (about 28 mmol) of DPPA in 150 ml of DMSO are stirred at room temperature for 2 hours, then 500 ml of ethyl acetate are added. The precipitated solid is collected (about 22 g) and used for the next step without any further purification.

Step c: Removal of the t-BOC-protective groups:

The crude product of step b is dissolved in 150 ml of dry TFA pre-cooled at 0° C., and the resulting solution is stirred at 0°–5°C. for 20 minutes. Then, 150 ml of methanol and 300 ml of diethyl ether are added. The precipitated solid is collected, washed several times with diethyl ether, and then it is purified by reverse-phase column chromatography (by combining only the fractions containing the pure desired individual factor) to yield 9 g of compound MA-A-3/B$_0$.

EXAMPLE 8

Preparation of compound 9 (RA-A-2) (Compound of formula(I) wherein Y is —CH$_2$OH, X is —NH—(CH$_2$)$_3$—[NH(CH$_2$)$_3$]$_2$—NH$_2$, R$_1$ is —H, R$_2$ is (C$_9$–C$_{12}$)alkyl corresponding to the factors of A 40926 complex, M is α-D-mannopyranosyl and Z is —H)

Step a:Preparation of N$^{15}$-(t-BOC)-RA, cyanomethyl ester

A solution of 8 g (about 4 mmol) of the compound of Example 2, step b, (N$^{15}$-(t-BOC)-RA), 0.75 ml (about 5.5 mol) of TEA and 8 ml of chloroacetonitrile in 40 ml of DMSO is stirred at room temperature for 5 hours. Then, 200 ml of ethyl acetate are added, and the precipitated solid is collected, yielding 8.2 of the crude cyanomethyl ester of the title.

Steps b and c: Condensation with N',N"-bis-(3-aminopropyl)-1,3-propanediamine and acidolysis of the t-BOC-protective group:

The crude cyanomethyl ester of step a is dissolved in 80 ml of DMSO and 9 g of N,N'-bis-(3-aminopropyl)-1,3-propanediamine is added. After stirring at room temperature for 20 hours, 320 ml of ethyl acetate are added. The precipitated solid is collected and re-dissolved in 70 ml of ice-cold dry TFA. The resulting solution is stirred at 0° C. for 10 minutes, and then 230 ml of cold diethyl ether are added. The precipitated solid is collected and re-dissolved quickly in 200 ml of water. The solution is adjusted at pH 5.5 with 1N NaOH and purified by reverse-phase chromatography (by combining all fractions containing the pure individual factors), yielding 1.3 of pure title compound RA-A-2.

EXAMPLE 9

Preparation of compound 10 (RA-A-3) (Compound of formula (I) wherein Y is —CH$_2$OH, X is —NH—(CH$_2$)$_3$—N[(CH$_2$)$_3$NH$_2$]$_2$, R$_1$ is H, R$_2$ is (C$_9$–C$_{12}$)alkyl corresponding to the factors of A 40926 complex, M is α-D-mannopyranosyl and Z is —H)

To a stirred solution of 9 g (about 5 mmol) in 100 ml of DMSO, 7 g (about 18 mmol) of N',N"-di(t-BoC)-tris-(3-aminopropyl)amine (Example 7, step a), 1.5 ml of TEA and 3 ml of DPPA are added at 10° C. After stirring at 10° C. for 1 hour and at room temperature for 4 hours, 400 ml of ethyl acetate are added. The precipitated solid (about 12 g) is re-dissolved in 80 ml of ice-cooled TFA and the resulting solution is stirred at 0°–5° C. for 10 minutes. Then, a mixture methanol/diethyl ether 1/1 (about 300 ml) pre-cooled at −10° C. is added. The precipitated solid is collected and quickly re-dissolved in 200 ml of water. The resulting solution is adjusted at pH 4 with 1N NaO and purified by reverse-phase chromatography (by combining all fractions containing the pure individual factors) to yield 1.8 g of the pure title compound RA-A-3.

EXAMPLE 10

Preparation of compound 11 (A-A-1) (Compound of formula (I) wherein Y is —COOH, X is —NH—(CH$_2$)$_3$—N(CH$_3$)$_2$, R$_1$ is —H, R$_2$ is (C$_9$–C$_{12}$)alkyl corresponding to the factors of A 40926 complex, M is α-D-mannopyranosyl and Z is —H)

To a stirred suspension of 5 g (about 2.5 mmol) of compound 6 (MA-A-1), prepared as described in Example 3, Method B, in 60 ml of tetrahydrofuran (THF), 10 ml of water and 20 ml of 1N NaOH are added at room temperature. After 30 minutes, the resulting solution is adjusted at pH 7 with 1N HC1, 150 ml of n-butane are added, and the mixture is concentrated to a small volume (about 20 ml), at 40° C. under reduced pressure. The solid precipitated by adding diethyl ether (about 200 ml) is collected (5.2 g) and purified by reverse-phase chromatography (by combining all fractions containing the pure individual factors), yielding 2.1 of the title compound A-A-1.

EXAMPLE 11

Preparation of compounds 12 (PyA-A-1) (Compound of formula (I) wherein Y is —COO$^⊖$, X is —NH—(CH$_2$)$_3$—N(CH$_3$)$_2$, R$_1$ is —H, R$_2$ is (C$_9$–C$_{12}$)alkyl corresponding to the factors of A 40926 complex, M is α-D-mannopyranosyl and Z is P$^⊕$(NC$_4$H$_8$)$_3$)

Compound 12 (PyA-A-1) is obtained from compound 7 (PyMA-A-1) of Example 4 by operating under the same conditions described in Example 10 for the preparation of compound 11 (A-A-1) from compound 6 (MA-A-1), with a 35% yield.

EXAMPLE 12

Preparation of compound 13 (A-A-3/B$_0$) (Compound of formula (I) wherein Y is —COOH, X is —NH—(CH$_2$)$_3$—N[(CH$_2$)$_3$NH$_2$]$_2$, R$_1$ is —H, R$_2$ is 9-methyldecyl, M is α-D-mannopyranosyl and Z is —H)

Compound 13 (A-A-3/B$_0$) is obtained from compound 5 (MA-A-3/B$_0$) of Example 7 under the same conditions described in Example 10 for the preparation of compound 11 (A-A-1) from compound 6 (MA-A-1), with a 41% yield.

EXAMPLE 13

Preparation of compound 14 (ABA-A-1) (Compound of formula (I) wherein Y is —CONHCH$_3$, X is —NH—(CH$_2$)—N(CH$_3$)$_2$, R$_1$ is —H, R$_2$ is (C$_9$–C$_{12}$)alkyl corresponding to the factors of A 40926 complex, M is α-D-mannopyranosyl and Z is —H)

Step a: Preparation of $N^{15}$-(t-BOC)-A-A-1, $6^B$-cyanomethyl ester

To a stirred solution of 22 g (about 11 mmol) of compound 11 (A-A-1) of Example 10 and 3 g of $NaHCO_3$ in 220 ml of water/dioxane 1/1 mixture, a solution of 5 g of di-tert-butyl-dicarbonate in 20 ml of dry dioxane is added dropwise at room temperature in 10 minutes. After stirring for 2 hours at room temperature, 200 ml of water are added, and then the resulting solution is adjusted at pH 3 with 1N HCl and extracted with 300 ml of n-butanol. The organic layer is separated and concentrated at 35° C. under reduced pressure to a small volume (about 45 ml). The solid precipitated by adding diethyl ether (about 250 ml) is collected (about 20 g of crude N15-(t-BOC)-A-A-1) and re-dissolved in 150 ml of DMSO. After adding 3 ml of TEA and 20 ml of chloroacetonitrile, the resulting solution is stirred at room temperature for 5 hours, and then 500 ml of ethyl acetate are added. The precipitated solid (about 18 g of the cyanomethyl ester) is enough pure for the use in the next step.

Step b: Reaction of the above $6^B$-cyanomethyl ester with methylamine and removal of the t-BOC-protective group A solution of 5 g of the above product in 75 ml of 25% (w/v) methylamine in ethanol is stirred at room temperature for 3 hours, and then 300 ml of diethyl ether are added. The precipitated solid (about 5.1 g) is collected and re-dissolved in 35 ml of TFA at 0° C. The resulting solution is stirred at 0° C. for 15 minutes, and then 50 ml of a methanol/diethyl ether 1/1 mixture are added to precipitate 4.5 g of crude product which is purified by reverse-phase column chromatography (by combining all fractions containing the pure individual factors), yielding 1.7 g of the title compound 14 (ABA-A-1).

EXAMPLE 14

Preparation of compound 15 (ADA-A-1) (Compound of formula (I) wherein Y is —CONH—$(CH_2)_3$—$N(CH_3)_2$, X is —NH—$(CH_2)_3$—$N(CH_3)_2$, $R_1$ is —H, $R_2$ is $(C_9$-$C_{12})$alkyl corresponding to the factors of A 40926 complex, M is α-D-mannopyranosyl and Z is —H)

A solution of 7 g (about 4 mmol) of antibiotic A 40926 complex, 2.5 ml (about 20 mmol) of 3,3-dimethylamino-1-propylamine, and 5.2 g (about 10 mmol) of PyBOP in 70 ml of DMF is stirred at room temperature for 1 hour, and then 400 ml of ethyl acetate are added.

The precipitated solid is collected and purified by reverse-phase chromatography (by combining all fractions containing the pure individual factors), yielding 2.1 g of the title compound 15 (ADA-A-1)

EXAMPLE 15

Preparation of compound 16 (PyRA-A-1) (Compound of formula (I) wherein Y is —$CH_2OH$, X is —NH—$(CH_2)_3$—$N(CH_3)_2$, $R_1$ is —H, $R_2$ is $(C_9$-$C_{12})$alkyl corresponding to the factors of A 40926 complex, M is α-D-mannopyranosyl and Z is $P^{\oplus}(NC_4H_8)_3$ $CH_3COO^{\ominus}$)

To a stirred solution of 400 mg (about 0.2 mmol) of compound 7 (PyMA-A-1) prepared as described in Example 4, in 20 ml of water, 4 ml of n-butanol and 200 mg of $NaBH_4$ are added at room temperature. After stirring at room temperature overnight, the reaction mixture is adjusted at pH 4.5 with glacial acetic acid and extracted with 50 ml of n-butanol. The organic layer is separated and the solvent is evaporated at 45° C. under reduced pressure. The solid residue is purified by reverse-phase chromatography (by combining all fractions containing the pure individual factors), to yield 175 mg of pure title compound 16 (PyRA-A-1)

EXAMPLE 16

Preparation of compound 25 (MA-A-4) (Compound of formula (I) wherein Y is —$COOCH_3$, X is

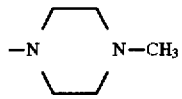

$R_1$ is —H, $R_2$ is $(C_9$-$C_{12})$alkyl corresponding to the factors of A 40926 complex, M is α-D-mannopyranosyl and Z is —H)

To a stirred solution of 5 g the compound of Example 1 (MA) in 60 ml of a DMF/DMSO 5/1 mixture, 0.3 ml of N-methyl-piperazine and 1.7 g of Py BOP are added at room temperature. After 1 hour-reaction, 140 ml of ethyl acetate are added, and the precipitated solid is collected and purified by reverse-phase column chromatography (by combining all fractions containing the pure individual components), yielding 1.9 g of the title compound MA-A-4.

EXAMPLE 17

Preparation of compound 24 (RA-A-4) (Compound of formula (I) wherein Y is —$CH_2OH$, X is

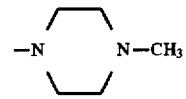

$R_1$ is —H, $R_2$ is $(C_9$-$C_{12})$alkyl corresponding to the factors of A 40926 complex, M is α-D-mannopyranosyl and Z is —H)

By following exactly the same procedure described in the above Example 16, under the same above reaction conditions, from 5 g of RA, 2.7 g of pure title compound RA-A-4 are obtained.

REVERSE-PHASE COLUMN CHROMATOGRAPHY

Pure samples of the above compounds are obtained by reverse phase column chromatography on silanized silica gel (0.063-0.2 mm; Merck). The crude product (for example, 0.5 g) is dissolved in a minimum amount of a mixture acetonitrile/water 1/1, then the solution is adjusted at pH 7 with 1N NaOH and diluted with water until a cloudy solution is formed. Afterwards, few drops of acetonitrile are added under vigorous stirring. As soon as a clear solution is obtained, this is loaded on a column of silanized silica gel (100 g) in water. Elution is carried out according to a linear gradient from 10% to 60% of acetonitrile in 0.1N acetic acid in 10 hours, at a flow rate of about 250 ml/hour, while collecting 20 ml/fractions which are checked by HPLC. Those fractions containing the pure compounds of formula (I) are selected and, when a complex compound wherein $R_2$ is $(C_9$-$C_{12})$alkyl corresponding to the factors of A 40926 complex is desired, all fractions containing pure factors are combined and the solvents are evaporated at 40° C. under reduced pressure in the presence of n-butanol to avoid foaming.

When in the process for preparing a compound of formula (I) antibiotic a 40926 complex has been used as the precursor and an individual factor of the amide compound of formula (I) is desired wherein $R_2$ corresponds to one of the meanings which characterize the individual factors of A 40926 complex (e.g. $R_2$ = 9-methyldecyl), only the fractions examined by HPLC which contain the desired pure factor are combined and treated as described above.

The identity and structure of each single factor of the compounds of this invention is determined by HPLC analysis of each reaction product. Accordingly, a preliminary identification of the desired factor is obtained by comparing the HPLC fingerprint of a 40926 complex with that of the crude reaction product (see, for instance, the HPLC pattern reported by L.F. Zerilli et al in "Rapid Communications in Mass Spectrometry, Vol. 6, 109, 1992) (in this paper factor $B_0$ of A 40926 complex is referred to as factor B).

HPLC analyses are performed on a column HIBAR (125×4mm; Merck) prepacked with LI-CHROSPHERE RP-8 (5 μm), using a Varian Model 5500 liquid chromatograph provided with a variable UV-detector. Chromatograms are recorded at 254 nm. Elutions are carried out according to a linear step-gradient from 20% to 60% of acetonitrile in 0.2% aqueous ammonium formate in 30 minutes at the flow rate of 1.5 ml/minute.

Since, in general, all complex compounds of this invention possess a typical HPLC fingerprint similar to that characteristic of the respective A 40926 complex precursor, the individual factors of the compound of this invention corresponding to those of the precursor A 40926 complex can be easily individuated by correlation of the two HPLC patterns. The eluted fractions of the reverse-phase chromatograms which contain said pure factors can be isolated and worked up as described above. For further confirmation of the identity of the $(C_9-C_{12})$alkyl chains a test sample of each fraction may be evaporated as described above to give a sample of product which can be examined by gas chromatography/mas spectrometry (GC/MS) according to the method described by L. F. Zerilli et al. in the paper mentioned above.

Table V reports the retention times ($t_R$) of the pure factor of each invention compound of formula (I) wherein $R_2$ is 9-methyldecyl (i.e. the one corresponding to factor $B_0$ of the A 40926 complex) which is taken as a reference in the reverse-phase purification procedures).

The table reports also the $t_R$ of the factor $B_0$ of A 40926 complex precursor and the corresponding ester starting material (MA) recorded under the same conditions described above.

TABLE V

| HPLC analysis | |
|---|---|
| Compound | $t_R$ (minutes) |
| A 40926 precursor | 9.7 |
| Starting material (MA) | 11.3 |
| compound 1 | 10.2 |
| compound 2 | 13.7 |
| compound 3 | 15.3 |
| compound 4 | 15.5 |
| compound 5 | 15.3 |
| compound 6 | 13.7 |
| compound 7 | 20.5 |
| compound 8 | 15.3 |
| compound 9 | 12.9 |
| compound 10 | 14.8 |
| compound 11 | 12.1 |
| compound 12 | 17.4 |
| compound 13 | 12.2 |
| compound 14 | 14.7 |
| compound 15 | 16.4 |
| compound 16 | 19.2 |

TABLE V-continued

| HPLC analysis | |
|---|---|
| Compound | $t_R$ (minutes) |
| compound 24 | 13.4 |
| compound 25 | 14.8 |

$^1$H- and $^{31}$P - NMR spectra $^1$H-NMR spectra at 500 MHZ are recorded in the temperature range from 20° C. to 30° C. on a Bruker AM 500 spectrometra in DMSO-$D_6$ with with tetramethylsilane (TMS) as the internal reference (delta=0.00 ppm). Table VI reports the most significant chemical shift (delta ppm) of some representative compounds.

TABLE VI

| Compound 1 (RA): | 0.85, 1.13, 1.42, 1.98 (acyl chain); 3.72 ($CH_2OH$), 4.05–6.22 (peptidic CH's); 6.43–8.52 (aromatic protons and peptidic NH's). |
|---|---|
| Compound 2 (MA-A-1/$B_0$): | 0.83, 1.14, 1.38, 1.99 (acyl chain), 1.83, 2.83 ($CH_2$-side chain), 2.73 ($N(CH_3)_2$); 4.11–6.10 (pepetidic CH's); 6.48–9.50 (aromatic protons and pepetidic NH's) |
| Compound 3 (RA-A-1/$B_0$): | 0.84, 1.14, 1.38, 1.92 (acyl chain); 1.72, 2.75 ($CH_2$-side chain); 2.53 ($N(CH_3)_2$); 3.69 ($CH_2$—OH); 4.09–6.11 (peptidic CH's); 6.41–9.18 (aromatic protons and peptidic NH's) |
| Compound 4 (MA-A-2/$B_0$): | 0.84, 1.15, 1.39, 1.98 (acyl chain); 1.96, 2.86 ($CH_2$-side chain); 4.08–6.15 (peptidic CH's); 6.42–9.61 (aromatic protons and NH's) |
| Compound 5 (M-A-3/$B_0$) | 0.85, 1.13, 1.42, 2.02 (acyl chain); 1.73, 2.82 (alkylamino chains); 2.42 (—N—$CH_3$); 3.63 ($COOCH_3$); 3.10–3.80 (sugars); 4.10–6.10 (peptidic CH's); 6.41–8.52 (aromatic protons and peptidic NH's) |
| Compound 7 (PyMA-A-1); | 0.84, 1.13, 1.42, 2.01 (acyl chains); 1.83, 2.16 (dimethylpropyl-amide); 2.32 (NH–$CH_3$); 1.70, 3.23 (pyrrolidine); 3.10–3.80 (sugars); 4.10–6.20 (peptidic CH's); 6.38–8.40 (aromatic protons and peptidic NH's) |
| Compound 9 (RA-A-2) | 0.84, 1.13, 1.39, 1.98 (acyl chains); 1.88, 2.91 (alkylamino chains); 2.41 (NH—$CH_3$); 3.10–3.80 (sugars); 4.10–6.10 (peptidic CH's); 6.38–8.49 (aromatic protons and peptidic NH's) |
| Compound 10 (RA-A-3): | 0.84, 1.13, 1,39, 1.98 (acyl chains); 1.73, 2.82 (alkylamino chains); 2.47 (NH—$CH_3$); 3.10–3.80 (sugars); 4.10–6.10 (peptidic CH's); 6.37–8.70 (aromatic protons and peptidic NH's); 9.2–10.4 (phenolic OH's) |
| Compound 11 (A-A-1): | 0.84, 1.13, 1.39, 2.00 (acyl chains); 1.74–2.79 (alkylamino chains); 2.37 (NH—$CH_3$); 3.10–3.80 (sugars); 4.10–6.10 (peptidic CH's); 6,39–8.50 (aromatic protons and peptidic NH's); |
| Compound 12 (PyA-A-1): | 0.84, 1.13, 1.42, 2.02 (acyl chains); 1.87, 2.73, 3.00 (dimethylpropylamide); 2.48 (NH—$CH_3$); 1.71, 3.30 (pyrrolidine); 3.10–3.80 (sugars); 4.10–6.25 (peptidic CH's); 6.38–8.55 (aromatic protons and peptidic NH's); |
| Compound 13 (A-A-3/$B_0$): | 0.84, 1.13, 1.42, 2.02 (acyl chains); 2.33 (NH—$CH_3$); 1.71, 2.80 (alkylamino chains); 3.10–3.80 (sugars); 4.10–6.10 (peptidic CH's); 6.37–8.50 (aromatic protons and peptidic NH's); |
| Compound 14 (ARA-A-1): | 0.84, 1.13, 1.42, 1.96 (acyl chains); 2.35 [(CH-NH)-$CH_3$)]; 1.78, 2.70 (alkylamino chains); 3.10–3.80 (sugars); 4.10–6.10 (peptidic CH's); 6.37–8.50 (aromatic protons and peptidic NH's); |

TABLE VI-continued

| Compound 15 (ADA-A-1): | 0.82, 1.13, 1.40, 1.98 (acyl chains); 2.50 (NH—CH$_3$); 1.72, 1.85, 2.73, 3.00 (alkylamino chains); 3.10–3.80 (sugars); 4.10–6.10 (peptidic CH's); 6.40–8.55 (aromatic protons and peptidic NH's); |
|---|---|
| Compound 16 (PyRA-A-1): | 0.84, 1.13, 1.41, 2.00 (acyl chains); 2.33 (NH—CH$_3$); 1.82, 2,16 (dimethylpropylamide); 1.71, 3.23 (pyrrolidine); 3.10–3.80 (sugars); 4.10–6.20 (peptidic CH's); 6.38–8.40 (aromatic protons and peptidic NH's); |
| Compound 24 (RA-A-4): | 0.84, 1.13, 1.40, 1.97 (acyl chains); 2.10 (piperazine CH$_3$); 2.38 (NH—CH$_3$); 3.10–3.80 (sugars); 4.05–6.07 (peptidic CH's); 6.38–8.49 (aromatic protons and peptidic NH's). |
| Compound 25 (MA-A-4): | 0.84, 1.13, 1.40, 2.00 (acyl chains); 2.13 (piperazine CH$_3$); 2.43 (NH—CH$_3$); 3.10–3.80 (sugars); 3.63 (COOCH$_3$); 4.05–6.09 (peptidic CH's); 6.38–8.49 (aromatic protons and peptidic NH's). |

$^{31}$P-NMR Spectra are recorded at 161.98 MHz (compound 12), or at 202.46 MHz (compounds 7 and 16) in DMSO-d$_6$ solution, with 85% H$_3$PO$_4$ as internal reference.
Compound 7 (PyMA-A-1) ($^{31}$p): one signal at delta 24.12 ppm
Compound 12 (PyA-A-1) ($^{31}$p): one signal at delta 23.50 ppm
Compound 16 (PyRA-A-1) ($^{31}$p): one signal at delta 24.11 ppm

We claim:
1. A derivative of antibiotic A 40926 of formula (I)

wherein
R$_1$ represents hydrogen or a protecting group of the amino function;

R$_2$ represents (C$_{10}$–C$_{11}$)alkyl;

M represents hydrogen, a-mannopyranosyl or 6-O-acetyl-α-D-mannopyranosyl;

Y represents (C$_1$–C$_4$)alkoxycarbonyl or hydroxymethyl;

X represents a compound of formula —NR$_3$—alk$_1$—(NR$_4$—alk$_2$)$_p$–(NR$_5$—alk$_3$)$_q$—W wherein:

R$_3$ represents hydrogen or (C$_1$–C$_4$)alkyl;

alk$_1$, alk$_2$ and alk$_3$ each independently represent a linear or branched alkylene of 2 to 10 carbon atoms;

p and q are integers which independently represent zero or 1;

R$_4$ and R$_5$ independently represent hydrogen atoms (C$_1$–C$_4$)alkyl or

R$_3$ and R$_4$ taken together represent a (C$_2$–C$_4$)alkylene moiety connecting the two nitrogen atoms with the proviso that p is 1; or R$_4$ and R$_5$ taken together represent a (C$_2$–C$_4$)alkylene moiety connecting the two nitrogen atoms with the proviso that both p and q are 1;

W represents hydrogen, (C$_1$–C$_4$)alkyl, amino, (C$_1$–C$_4$) alkylamino, di(C$_1$–C$_4$)alkylamino, amino substituted with one or two amino(C$_2$–C$_4$)alkyl moieties or with one or two (C$_1$–C$_4$)alkylamino-(C$_2$–C$_4$)alkyl moieties or with one or two di(C$_1$–C$_4$)alkylamino-(C$_2$–C$_4$)alkyl moieties, and the pharmaceutically acceptable addition salts thereof.

2. An antibiotic substance as in claim 1 wherein R$_2$ represents 9-methyldecyl, M represents α-D-mannopyranosyl and R$_1$, X and Y are as in claim 1.

3. An antibiotic substance as in claim 1 wherein

R$_2$ represents 9-methyldecyl

Y represents methoxymethyl or hydroxymethyl and

X is selected from
—NH—(CH$_2$)$_3$—N(CH$_3$)$_2$.
—NH—(CH$_2$)$_3$—[NH—(CH$_2$)$_3$]$_2$—NH$_2$ and
—NH—(CH$_2$)$_3$—N[(CH$_2$)$_3$NH$_2$]$_2$.

4. A pharmaceutical composition containing a compound of claim 1 as the active ingredient in admixture with a pharmaceutically acceptable carrier.

5. A method for the treatment of bacterial infections comprising administering a compound according to claim 1 to patient in need thereof.

* * * * *